(12) United States Patent
Hicks et al.

(10) Patent No.: US 9,677,139 B2
(45) Date of Patent: Jun. 13, 2017

(54) GENETIC MARKERS INDICATIVE OF A CANCER PATIENT RESPONSE TO TRASTUZUMAB (HERCEPTIN)

(75) Inventors: James Hicks, Huntington, NY (US); Alexander Krasnitz, Huntington, NY (US)

(73) Assignee: COLD SPRING HARBOR LABORATORY, Cold Spring Harbor, NY (US)

( * ) Notice: Subject to any disclaimer, the term of this patent is extended or adjusted under 35 U.S.C. 154(b) by 0 days.

(21) Appl. No.: 13/491,359

(22) Filed: Jun. 7, 2012

(65) Prior Publication Data

US 2012/0328607 A1 Dec. 27, 2012
US 2016/0340735 A9 Nov. 24, 2016

Related U.S. Application Data

(63) Continuation-in-part of application No. PCT/US2010/059846, filed on Dec. 10, 2010.

(60) Provisional application No. 61/495,827, filed on Jun. 10, 2011, provisional application No. 61/285,933, filed on Dec. 11, 2009.

(51) Int. Cl.
*C12Q 1/68* (2006.01)
*A61K 39/395* (2006.01)
*A61K 31/337* (2006.01)
*A61K 39/00* (2006.01)

(52) U.S. Cl.
CPC .......... *C12Q 1/6886* (2013.01); *A61K 31/337* (2013.01); *A61K 39/39558* (2013.01); *A61K 2039/545* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,569,617 B1 | 5/2003 | Wigler et al. | |
| 7,531,307 B2 | 5/2009 | Wigler et al. | |
| 8,273,871 B2 | 9/2012 | Hannon et al. | |
| 2005/0032095 A1 | 2/2005 | Wigler et al. | |
| 2005/0266444 A1 | 12/2005 | Wigler et al. | |
| 2005/0287543 A1 | 12/2005 | Yu et al. | |
| 2006/0257895 A1* | 11/2006 | Pinkel et al. | 435/6 |
| 2007/0161008 A1 | 7/2007 | Morrison et al. | |
| 2007/0207481 A1 | 9/2007 | Wigler et al. | |
| 2009/0280493 A1 | 11/2009 | Wirtz | |
| 2010/0227768 A1 | 9/2010 | Wigler et al. | |
| 2012/0149593 A1 | 6/2012 | Hicks et al. | |
| 2013/0179999 A1 | 7/2013 | Hannon et al. | |

FOREIGN PATENT DOCUMENTS

WO 2008/154249 12/2008
WO WO 2012/054873 4/2012

OTHER PUBLICATIONS

National Library of Medicine, National Institutes of Health. Genetics Home Reference. Chromosome 5 (Bethesda, MD, USA), available via url: <ghr.nlm.nih.gov/chromosome/5#ideogram> printed on Apr. 7, 2014.*
National Library of Medicine, National Institutes of Health. NCBI Map viewer for chromosome 5 (Bethesda, MD, USA), available via url: <ncbi.nlm.nih.gov/mapview/maps.cgi?org=human &maps=ideogr,morbid,pheno&zoom=100&chr=5>, printed on Apr. 7, 2014.*
UCSC Genome Browser on Human Mar. 2006 (NCBI36/hg18) Assembly, available via url: <genome.ucsc.edu/cgi-bin/hgGateway?db=hg18>, printed on Apr. 7, 2014.*
National Center for Biotechnology Information, National Library of Medicine, OMIM Database for the ERBB2 gene (Bethesda, MD, USA), available via url: <omim.org/entry/164870>, p. 1, printed on Apr. 8, 2014.*
Baumbusch et al BMC Genomics. Aug. 8, 2008. 9: 379.*
Seidman et al J Clin Oncology. 2008. 26(10):1642-1649.*
Aug. 30, 2011 International Search Report, issued in connection with PCT International Application No. PCT/US2010/059846, of which the subject application claims benefit.
Jun. 12, 2012 International Preliminary Report on Patentability, issued in connection with PCT International Application No. PCT/US2010/059846, of which the subject application claims benefit.
Gullo et al., "Level of HER2/neu gene amplification as a predictive factor of response to trastuzumab-based therapy in patients with HER2-positive metastatic breast cancer" Ingest New Drugs, (2008) 27(2):179-183.
Moelans et al., "Absence of chromosome 12 polysomy in breast cancer: analysis by CEP17 chromogenic in situ hybridization and multiplex ligation-dependent probe amplification" Breast Cancer Res. Treat., (2009) 120:1-7.
Morrison et al., "Effects of ERBB2 amplicon size and genomic alterations of chromosomes 1, 3, and 10 on patient response to trastuzumab in metastatic breast cancer" Genes Chromosomes Cancer (2007) 46(4):397-405 (Abstract Only).

* cited by examiner

*Primary Examiner* — Carla Myers
(74) *Attorney, Agent, or Firm* — Gary J. Gershik; Cooper & Dunham LLP

(57) ABSTRACT

The invention relates to the fields of therapeutics and identifying candidates for therapy, in particular to a method of identifying candidates for trastuzumab (Herceptin®) therapy in a patient presenting with breast cancer based on the presence or absence of specific genetic markers in a tumor sample from said patient.

4 Claims, 24 Drawing Sheets

Genotyping Distribution in 9840/9342 vs an Early Stage Cohort

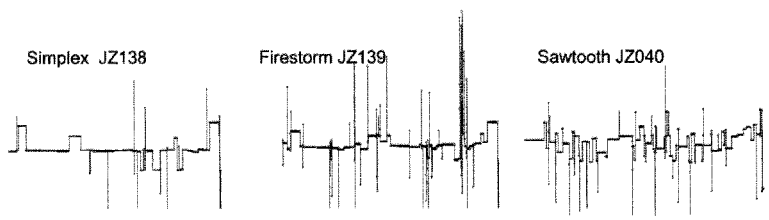

| Pseudo-diploid | Freq in 9840 | Freq in 9342 | Approx. freq. expect for unselect. set | Notes |
|---|---|---|---|---|
| Simplex w/Her2 amp | 2/162 (1.2%) | 0/54 | <1% | LumA-like |
| Simplex Her2 norm | 2/162 (1.2%) | 3/54 (5.7%) | 24% | LumA-like |
| Sawtooth w/Her2 amp | 1/162 (0.6%) | 0/54 | <1% | Basal-like/ LumB |
| Sawtooth Her2 norm | 1/162 (0.6%) | 1/54 (1.9%) | 4% | Basal-like/Her2 |
| Firestorm w/Her2 amp | 1/162 (0.6%) | 6/54 (11.4%) | 10% | Her2 |
| Firestorm Her2 norm | 1/162 (0.6%) | 4/54 (7.8%) | 10% | LumB-like |
| Aneuploid/Polyploid | | | | |
| Simplex w/Her2 amp | 2/162 (1.2%) | 0/54 | <1% | LumA/Her2 like |
| Simplex Her2 norm | 2/162 (1.2%) | 0/54 | <1%% | Normal-like |
| Sawtooth w/Her2 amp | 5/162 (3.1%) | 1/54 (1.9%) | 9% | Basal/Her2 |
| Sawtooth Her2 norm | 24/162 (14.8%) | 9/54 (16.7%) | 15% | Basal-like |
| Firestorm w/Her2 amp | 30/162 (18.5%) | 5/54 (9.3%) | 10% | Her2/LumB-like |
| Firestorm Her2 norm | 59/162 (36.4%) | 15/54 (27.8%) | 14% | LumB-like |
| Too complex to call | 8 | 9 | | |

Figure 5

GENETIC MARKERS INDICATIVE OF A CANCER PATIENT RESPONSE TO TRASTUZUMAB (HERCEPTIN)

This application is a continuation-in-part of PCT International Application No. PCT/US10/59846, filed Dec. 10, 2010, claiming priority of U.S. Provisional Application No. 61/285,933, filed Dec. 11, 2009; and also claims the benefit of U.S. Provisional Application No. 61/495,827, filed Jun. 10, 2011, the entire contents of each of which are hereby incorporated by reference in their entireties.

Throughout this application, various publications are referenced by full citation. The disclosures of these publications in their entireties are hereby incorporated by reference into this application to more fully describe the state of the art to which this invention pertains.

REFERENCE TO A SEQUENCE LISTING

This application incorporates-by-reference nucleotide and/or amino acid sequences which are present in the file named "170130_82936_A_Sequence_Listing_JJC.txt", which is 19,589 kilobytes in size, and which was created Jan. 17, 2017 in the IBM-PC machine format, having an operating system compatibility with MS-Windows, which is contained in the text file filed Jan. 30, 2017.

FIELD OF THE INVENTION

The invention relates to the fields of therapeutics and identifying candidates for therapy, in particular to a method of identifying candidates for trastuzumab (Herceptin®) therapy in a patient presenting with breast cancer based on the presence or absence of specific genetic markers in a tumor sample from said patient.

BACKGROUND OF THE INVENTION

As of 2007, an estimated 1.3 million new cases of invasive breast cancer were expected to occur among women and an estimated 465,000 breast cancer deaths in women were expected to occur. Breast cancer is the most frequently diagnosed cancer in women and it is the leading cause of cancer death among women worldwide. (ACS 2007 Stats).

Up to 25% of women who present with early breast cancer have developed tumors which overexpress human epidermal growth factor receptor 2 (Her2/neu), usually as a result of erbB2 gene amplification. (Owens M A at al. Clin. Breast Cancer 5 (2004)). These tumors are considered to be Her2+ and are characterized by aggressive growth and division, which can result in high recurrence rates after initial treatment and poor prognosis. (Slamon D J, Clark G M, Wong S G, Levin W J, Ullrich A, McGuire W L. Human breast cancer: correlation of relapse and survival with amplification of the Her2/neuoncogene. Science, 1987; 235: 177-182).

One method to test for Her2+ tumors is to use immunohistochemistry (IHC) to measure the levels of receptor on cancer cell surfaces. The test is scored on a scale of 0 to 3+, where a score of 0=negative, 1+=negative, 2+=borderline, or 3+=positive based on a reviewer's interpretation of staining intensity and completeness of membrane staining.

Additionally, Her2 gene amplification is detected using a fluorescent in situ hybridization (FISH) test that quantifies the number of gene copies in the cancer cell nucleus. A number of reports have verified its accuracy both in freshly frozen and paraffin-embedded tumor material (Mitchell, M. S., *Semin. Oncol,* 26:108 (1999))). FISH is generally performed using either single-color (HER-2/neu probe only) or dual-color hybridization (using HER-2/neu and control probes (e.g., chromosome 17 centromere probes simultaneously), with the latter method making it easier to distinguish true HER-2/neu amplification from chromosomal aneuploidy. FISH using entire cells (e.g., cultured cells, pulverized tissue, or imprint touch specimens from tumors) is considered straightforward, but the use of tissue sections complicates the quantitative nature of FISH due to nuclear truncation (i.e., due to the slicing of the tissues during their preparation for staining).

Chromogenic in situ hybridization (CISH) operates according to the same principles as FISH, except polynucleotide probes are labeled with a chromogen rather than a fluorophore. CISH does not require a costly fluorescent microscope and CISH signals do not decay over time.

Trastuzumab (Herceptin®) was developed as a targeted therapy to combat Her2 overexpression. Trastuzumab is a humanized monoclonal antibody directed against the extracellular domain of Her2 and is therefore specific for its target. Trastuzumab is approved for the adjuvant treatment of Her2-overexpressing node-positive or node-negative breast cancer. Trastuzumab in combination with paclitaxel is approved for the first-line treatment of Her2-overexpressing metastatic breast cancer. Trastuzumab as a single agent is approved for treatment of Her2-overexpressing breast cancer in patients who have received one or more chemotherapy regimens for metastatic disease. Trastuzumab has been shown to be effective across all of its approved uses (C. Jakisch, Her2-positive metastatic breast cancer: optimizing trastuzumab-based therapy, Oncologist 11 (2006) 34-41; Gonzalez-Angulo, G. N. Hortobagyi, F. J. Esteva, Adjuvant therapy with trastuzumab for Her2/neu-positive breast cancer, Oncologist 11 (2006) 857-867; C. A. Hudis, Trastuzumab-mechanism of action and use in clinical practice. N. Engl. J. Med. 357 (1) (Jul. 5, 2007) 39-51.).

Unfortunately, not all patients with Her2+ tumors are responsive to trastuzumab treatment. Trastuzumab monotherapies only lead to tumor regression in approximately 30% of patients. Complicating the issue further is the fact that administration of trastuzumab with anthracyclines and cyclophosphamide, while effective, leads to cardiac events in 28% of the patients. (T. M. Suter. N. Cook-Bruns, C. Barton, Cardiotoxicity associated with trastuzumab (Herceptin) therapy in the treatment of metastatic breast cancer, Breast 13 (3) (June 2004) 173-183). Additionally, a trastuzumab-containing treatment regimen is expensive, costing up to $100,000 per year. Thus, in an effort to reduce dangerous side effects and provide the most effective treatment, it is imperative to further refine the process by which trastuzumab is prescribed to try to better identify who will be sensitive to treatment.

Currently, because of the cost and risk associated with trastuzumab treatment, only subjects that have Her2+ tumors are administered the drug. Amongst these trastuzumab-treated Her2+ patients, up to 30-50% of patients will not positively respond to the treatment. Furthermore, it is currently thought that patients with Her2− tumors will not benefit from trastuzumab treatment. Nonetheless, despite the response rate in Her2+ patients, and the unknown effects of treatment in Her2− patients, trastuzumab treatment decisions are currently based on the detection of elevated Her2 levels. The discovery of additional markers could improve treatment decisions and identify Her2− subjects who could benefit from receiving trastuzumab, while also refining the number of Her2+ subjects to those who could best benefit from treatment.

SUMMARY OF THE INVENTION

In a first aspect, the invention relates to a process of producing information indicative of whether a human cell has a deletion at human chromosome region Chr18:309355-76106388 (marker D3), a deletion at human chromosome region Chr15:20444124-88087873 (marker D1), a deletion at human chromosome region Chr8:2780282-31010773 (marker D26), a deletion at human chromosome region Chr17:1612008-46199917 (marker D31), a deletion at human chromosome region Chr18:44824169-76106388 (marker D57), a deletion at human chromosome region Chr17:36157799-41605371 (marker D58), an amplification at human chromosome region Chr11:5755441-5766622 (marker A1), an amplification at human chromosome region Chr11: 5755441-5756473 (marker A73) or an amplification at human chromosome region 4q169.81-q185.239 (marker B), comprising determining by apparatus a copy number for marker D3, marker D11, marker D26, marker D31, marker D57, marker D58, marker A1, marker A73, or marker B, thereby producing information indicative of whether human cell has a deletion at marker D3, a deletion at marker D11, a deletion at marker D26, a deletion at marker D31, a deletion at marker D57, a deletion at marker D58, an amplification at marker A1, an amplification at marker A73, or an amplification at marker B.

In a second aspect, the invention relates to a process for identifying a human subject as a candidate for trastuzumab therapy comprising determining by apparatus a copy number of human chromosome region Chr18:309355-76106388 (marker D3), human chromosome region Chr15:20444124-88087873 (marker D11), human chromosome region Chr8:2780282-31010773 (marker D26), human chromosome region Chr17:1612008-46199917 (marker D31), human chromosome region Chr18:44824169-76106388 (marker D57), human chromosome region Chr17:36157799-41605371 (marker D58), human chromosome region Chr11:5755441-5766622 (marker A1), human chromosome region Chr11:5755441-5756473 (marker A73) or human chromosome region 4q169.81-q185.239 (marker B) in a cancer cell of the subject, and identifying the subject as a candidate for trastuzumab therapy if the copy number data of step a) is indicative of a deletion at marker D3, a deletion at marker D11, a deletion at marker D26, a deletion at marker D31, a deletion at marker D57, a deletion at marker D58, an amplification at marker A1, an amplification at marker A73, or an amplification at marker B.

In a third aspect, the invention relates to a method of treating a human subject afflicted with cancer comprising a) obtaining information indicative of whether the human subject is a candidate for trastuzumab therapy, the information based on a copy number of human chromosome region Chr18:309355-76106388 (marker D3), human chromosome region Chr15:20444124-88087873 (marker D11), human chromosome region Chr8:2780282-31010773 (marker D26), human chromosome region Chr17:1612008-46199917 (marker D31), human chromosome region Chr18:44824169-76106388 (marker D57), human chromosome region Chr17:36157799-41605371 (marker D58), human chromosome region Chr1:5755441-5766622 (marker A1), human chromosome region Chr11:5755441-5756473 (marker A73) or human chromosome region 4q169.81-q185.239 (marker B), wherein the subject is a candidate for trastuzumab therapy it the copy number data is indicative of a deletion at marker D3, a deletion at marker D11, a deletion at marker D26, a deletion at marker D31, a deletion at marker D57, a deletion at marker D58, an amplification at marker A1, an amplification at marker A73, or an amplification at marker B; and b) if the information indicates that the human subject is a candidate for trastuzumab therapy, then administering to the human subject an amount of trastuzumab effective to treat the human subject afflicted with cancer.

In a fourth aspect, the invention relates to a kit for identifying a subject's sensitivity to trastuzumab therapy, said kit comprising one or more nucleic acid probes each of which selectively bind to a target polynucleotide sequence of the chromosome region comprising one of human chromosome region Chr18:309355-76106388 (marker D3), human chromosome region Chr15:20444124-88087873 (marker D11), human chromosome region Chr8:2780282-31010773 (marker D26), human chromosome region Chr17: 1612008-46199917 (marker D31), human chromosome region Chr18:44824169-76106388 (marker D57), human chromosome region Chr17:36157799-41605371 (marker D58), human chromosome region Chr11:5755441-5766622 (marker A1), human chromosome region Chr11:5755441-5756473 (marker A73) or human chromosome region 4q169.81-q185.239 (marker B) under conditions in which the probe forms a stable hybridization complex with the target polynucleotide sequence.

In a fifth aspect, the invention relates to a method of identifying a genomic marker comprising: a) obtaining a set of genomic copy number profiles; b) deriving from the set of genomic copy number profiles a set of N copy number events $A_j$, wherein j=1, . . . , N and wherein each copy number event is associated with a specific interval of the genome and a real number $U_j$, wherein $0 \leq U_j \leq 1$; c) setting $U_j$ to 1; d) determining for each copy number event $A_j$ and an interval I an explanation value $E_j(I)$, wherein $E_j(I)=U_j L(I)/L(A_j)$ if I is contained in $A_j$ and $E_j(I)=0$ if I is not contained in Aj, and wherein L(I) is the length of interval I and $L(A_1)$ is the length of copy number event $A_j$; e) summing the values determined in step (d) for interval I to provide an explanation of the set of copy number events, E(I); f) determining an optimal explanation value S of the set of copy number events and a corresponding optimal explaining interval C, wherein S=max$_I$E(I) and wherein C=argmax$_I$E (I); g) updating $U_j$ by subtracting the value of C determined in step (f) for all j=1, . . . , N; h) repeating step (d) through step (g) at least one times and i) selecting an optimal explaining interval whose optimal explanation value is statistically significant, thereby identifying an optimal explaining interval as a genomic marker.

In a sixth aspect, the invention relates to a process of producing information indicative of whether a human cell has a deletion at chromosome region 17q35.42-q56.76, a deletion at human chromosome region 17q32.010-q32.34.215 or an amplification at human chromosome region 4q169.81-q185.239, comprising determining by apparatus a copy number for 17q35.42-q56.76, 17q32.010-q32.34.215 or 4q169.81-q185.239, thereby producing information indicative of whether human cell has a deletion at 17q35.42-q56.76, a deletion at human 17q32.010-q32.34.215 or an amplification at 4q169.81-q185.239.

In a seventh aspect, the invention relates to a process for identifying a human subject as a candidate for trastuzumab therapy comprising determining by apparatus a copy number of human chromosome region 17q35.42-q56.76, human chromosome region 17q32.010-q32.34.215 or human chromosome region 4q169.81-q185.239 in a cancer cell of the subject; and identifying the subject as a candidate for trastuzumab therapy if the copy number data is indicative of a deletion at 17q35.42-q56.76, a deletion at 17q32.010-q32.34.215 or an amplification at 4q169.81-q185.239.

In an eighth aspect, the invention relates to a method of treating a human subject afflicted with cancer comprising obtaining information indicative of whether the human subject is a candidate for trastuzumab therapy, the information based on a copy number of human chromosome region 17q35.42-q56.76, human chromosome region 17q32.010-q32.34.215 or human chromosome region 4q169.81-q185.239, wherein the subject is a candidate for trastuzumab therapy if the copy number data is indicative of a deletion at 17q35.42-q56.76, a deletion at 17q32.010-q32.34.215 or an amplification at 4q169.81-q185.239; and if the information indicates that the human subject is a candidate for trastuzumab therapy, then administering to the human subject an amount of trastuzumab effective to treat the human subject afflicted with cancer.

In a ninth aspect, the invention relates to a kit for identifying a subject's sensitivity to trastuzumab therapy, said kit comprising one or more nucleic acid probes each of which selectively bind to a target polynucleotide sequence of the chromosome region comprising one of human chromosome region 17q35.42-q56.76, human chromosome region 17q32.010-q32.34.215 or human chromosome region 4q169.81-q185.239 under conditions in which the probe forms a stable hybridization complex with the target polynucleotide sequence.

BRIEF DESCRIPTION OF THE FIGURES

FIG. 1. Comparison of aCGH measures of Her2 copy number with Her2 FISH and mRNA expression.

FIG. 3. Plots of trastuzumab response (treated vs. untreated) plotted as overall survival (y axis) over time in months (x axis) for various combinations of markers demonstrating that amplifications or deletions at particular markers are associated with an increased sensitivity to trastuzumab.

FIG. 68. Deletions of BRCA1 identify response to Trastuzumab among cases NOT amplified for ERBB2. Survival (y axis) measured over months (x axis).

DETAILED DESCRIPTION OF THE INVENTION

Figure 1A:
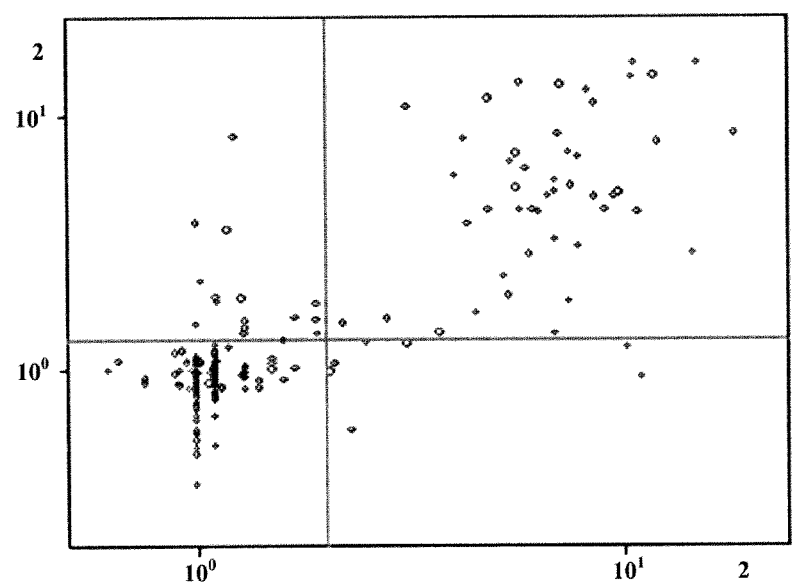
FIG. 1A. Her2 CGH values (y axis) plotted against Her2 FISH values (x axis). Threshold values (gray lines) for positivity are 1.3 for CGH and 2.0 for FISH.
Figure 1B:
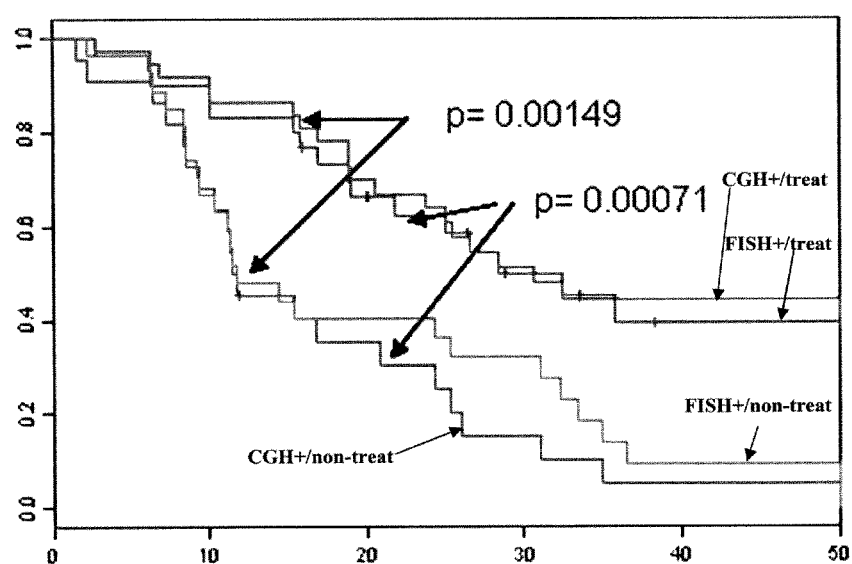
FIG. 1B. Plot of trastuzumab response measured as overall survival (treated vs. untreated) (y axis) over time in months (x axis) for patients assayed as positive by FISH or by CGH.
Figure 1C:
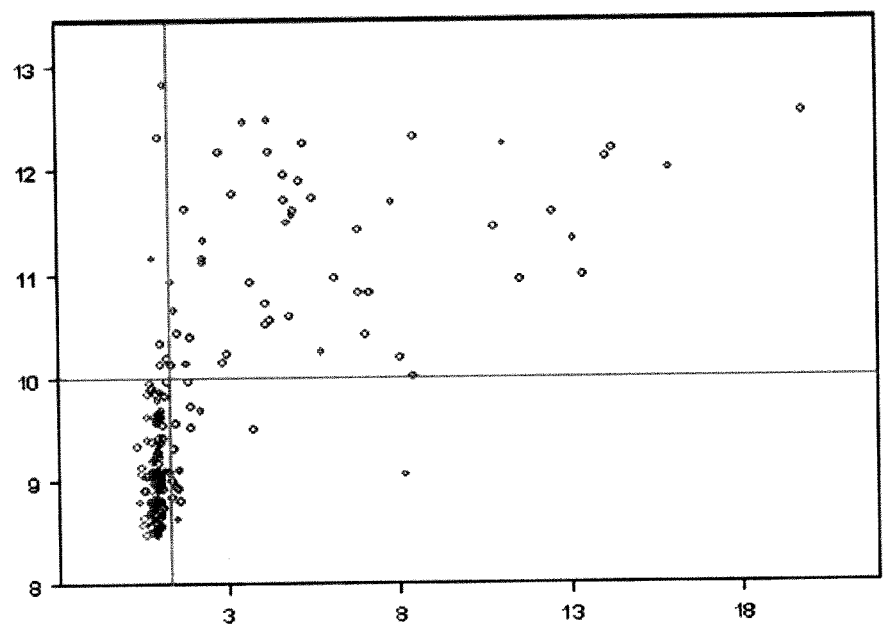
FIG. 1C. Scatterplot of Her2 mRNA expression (y axis) compared to FISH copy number (x axis). Threshold value for overexpression set at 10 (gray line).
Figure 1D:
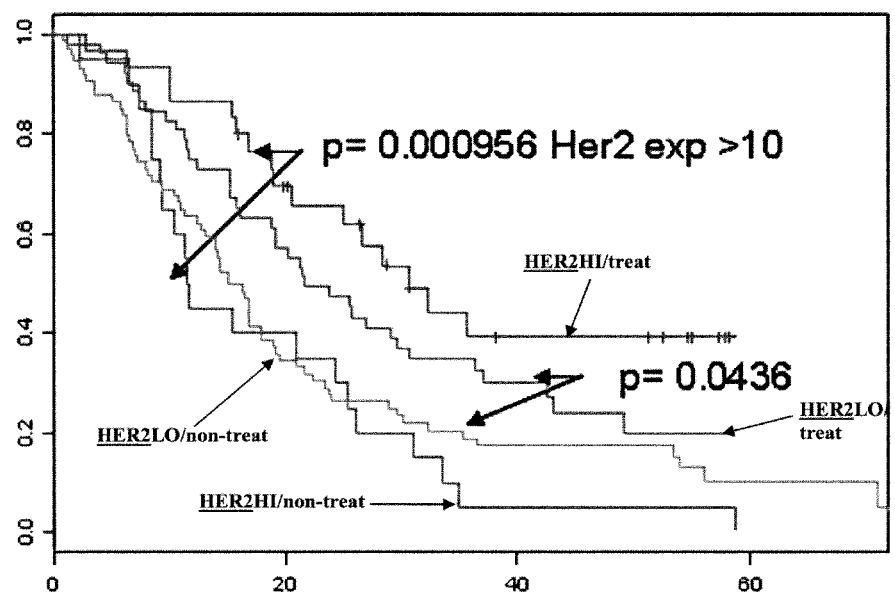
FIG. 1D. Plot of trastuzumab response measured as overall survival (treated vs. untreated) (y axis) over time in months (x axis) for patients with Her2 expression >10 ("HER2HI") compared to patients with expression <10 ("HER2LO").

In order to facilitate the understanding of the invention described in this patent application, the meaning of some terms and expressions in the context of the invention are explained below: As used herein, the term "amplification" or "amplified" when each refers to a genomic region indicates that such genomic region is present in the genomic DNA at a higher copy number than the mean copy number of the remainder of the genome.

As used herein, the term "candidate for trastuzumab therapy" refers to a human that is suspected of having cancer that may be evaluated for suitability for trastuzumab treatment. Examples of candidate subjects include, but are not limited to, human women suspected of having breast cancer and human men suspected of having breast cancer.

The term "sample" as used herein, relates to any sample which can be obtained from the patient. The present method can be applied to any type of biological sample from a patient, such as a biopsy sample, tissue, cell or fluid (serum, saliva, semen, sputum, cerebral spinal fluid (CSF), tears, mucus, sweat, milk, brain extracts and the like). In a particular embodiment, said sample is a tumour tissue sample or portion thereof. In a more particular embodiment, said tumor tissue sample is a breast tumor tissue sample from a patient suffering from breast cancer. Said sample can be obtained by conventional methods, e.g., biopsy, by using methods well known to those of ordinary skill in the related medical arts. Methods for obtaining the sample from the biopsy include gross apportioning of a mass, or microdissection or other art-known cell-separation methods. Tumour cells can additionally be obtained from fine needle aspiration cytology. In order to simplify conservation and handling of the samples, these can be formalin-fixed and paraffin-embedded or first frozen and then embedded in a cryosolidifiable medium, such as OCT-Compound, through immersion in a highly cryogenic medium that allows for rapid freeze. The samples may be obtained from subjects previously diagnosed with breast cancer (patients), or from subjects who have not been previously diagnosed with breast cancer, or from patients diagnosed with breast cancer who are undergoing treatment, or from subjects diagnosed with breast cancer who have been previously treated.

As used herein, the term "copy number" as used in reference to specific nucleic acid sequences (e.g., Her2/neu, marker D3, marker D11, marker D26, marker D31, marker D57, marker D58, marker A1, marker B and control) refers to the actual number of these sequences per single cell. Copy number may be reported for one single cell, or reported as the average number in a group of cells (e.g., tissue sample). When comparing the "copy number" of cells (e.g., experimental and control cells) one need not determine the exact copy number of the cell, but instead need only obtain an approximation that allows one to determine whether a given cell contains more or less of the nucleic acid sequence as compared to another cell. Thus, any method capable of reliably directly or indirectly determining amounts of nucleic acid may be used as a measure of copy number even if the actual copy number is not determined. In an embodiment, copy number can be represented as the ratio of hybridization signal at any locus in the genome comparing a tumor DNA sample to a DNA sample from a standard diploid reference.

As used herein, the term "Her2" refers to a nucleic acid sequence encoding the Human epidermal growth factor receptor 2 (Her2) protein, and includes both the wild-type sequence and naturally occurring variations, truncations, and mutations. Her2 is also known as "HER2," "Her-2," "Her-2/neu," "neu," "ErbB-2," and "ERBB2," all of which terms are encompassed herein in "Her2."

As used herein, the term "apparatus" refers to any methods, assays or equipment used to determine copy number of one or more genomic regions of a chromosome. Methods may include polymerase chain reaction (PCR), quantitative PCR, Southern Blotting, in situ hybridization techniques (ISH) (e.g., fluorescent in situ hybridization (FISH) or chromogenic in situ hybridization (CISH)), comparative genomic hybridization (CGH), array comparative genomic hybridization (aCGH), representational oligonucleotide microarray analysis (ROMA) and any other techniques used to determine copy number readily available and known to those of skill in the art. Equipment may include DIC microscope, fluorescent microscope, microarrays, slide scanners, computer software, computer algorithms and any other equipment used to determine copy number of a genomic region.

As used herein, the term "indicative of the subject's sensitivity to trastuzumab therapy", refers to a subject that is either Her2+, has a deletion at marker D3, a deletion at marker D11, a deletion at marker D26, a deletion at marker D31, a deletion at marker D57, a deletion at marker D58, an amplification at marker A1, an amplification at marker A73, an amplification at marker B, a deletion at marker D1, a deletion at marker D2, or has any combination or permutation of one, two three, four, five, six, seven, eight, nine, ten, eleven or twelve of the events.

As used herein, the term "amplification" when used in reference to copy number refers to the condition in which the copy number of a nucleic acid sequence (e.g., Her2) is greater than the copy number of a control sequence (e.g., chromosome 17). In other words, amplification indicates that the ratio of a particular nucleic acid sequence (e.g., Her2) is greater than 1:1 when compared to a control sequence (e.g., 1.1:1, 1.2:1, or 1.3:1).

As used herein, the term "deletion" when used in reference to copy number refers to the condition in which the copy number of a nucleic acid sequence (e.g., Her2) is less than the copy number of a control sequence (e.g., chromosome 17). In other words, amplification indicates that the ratio of a particular nucleic acid sequence (e.g., Her2) is less than 1:1 when compared to a control sequence (e.g., 0.25:1, 0.50:1, or 0.85:1).

As used herein, the term 'nucleic acid' refers to any nucleic acid containing molecule including, but not limited to DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine. N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine. N6-methyladenine, 7-methylguanine, 5-methylaminomethyluracil, 5-methoxyaminomethyl-2-thiouracil, beta-Dmannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5- oxyacetic acid methylester, uracil-5-oxyacetic acid, pseudouracil, queosine, 2-thiocytosine, and 2,6-diaminopurine.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the melting temperature of the formed hybrid, and the G:C ratio within the nucleic acids.

As used herein, the term "probe" refers to an oligonucleotide (i.e., a sequence of nucleotides), whether occurring naturally as in a purified restriction digest or produced synthetically, recombinantly or by amplification (e.g. PCR), which is capable of hybridizing to another oligonucleotide of interest. Probes useful in the present invention may be single-stranded or double-stranded. Probes are useful in the detection, identification and isolation of particular gene sequences (e.g., Her2, marker A1, marker A2 or marker B). It is contemplated that any probe used in the present invention may be labeled with any "reporter molecule," so that is detectable in any detection system, including, but not limited to enzyme (e.g., ELISA, as well as enzyme-based immunohistochemical assays), fluorescent (e.g., FISH), radioactive, mass spectroscopy, and luminescent systems. It is not intended that the present invention be limited to any particular detection system or label.

As used herein, the term "label" refers to any molecule which may be detected. For example, labels include, but are not limited to, 32P, 14C, 125I, 3H, 35S, biotin, digoxigenin, avidin, fluorescent or enzymatic molecules.

The reference genome referred to as freeze HG 18 is the March 2006 human reference sequence (NCBI Build 36.1) which was produced by the International Human Genome Sequencing Consortium (Nature. (2001) February 15; 409 (6822):860-921; Kuhn et al., "The UCSC Genome Browser database: update 2007." Nucleic Acids Res. (2007) January; 35 (Database issue):D668-D673; Fujita at al., "The UCSC Genome Browser database: update 2011." Nucleic Acids Res. (2011) 39 (suppl 1): D876-D882.) The HG18 reference genome data is publicly available at: genome.ucsc.edu/cgi-bin/hgGateway?db=hg1 8. As used herein, "as defined by the freeze HG18 reference genome", refers to the numbering of chromosomal positions set forth based on the human reference genome HG18, NCBI Build 36.1.

A process is provided for producing information indicative of whether a human cell has a deletion at human chromosome region Chr18:309355-76106388 (marker D3), a deletion at human chromosome region Chr15:20444124-88087873 (marker D11), a deletion at human chromosome region Chr8:2780282-31010773 (marker D26), a deletion at human chromosome region Chr17:1612008-46199917 (marker D31), a deletion at human chromosome region Chr18:44824169-76106388 (marker D57), a deletion at human chromosome region Chr17:36157799-41605371 (marker D58), an amplification at human chromosome region Chr11:5755441-5766622 (marker A1), an amplification at human chromosome region Chr11:5755441-5756473 (marker A73) or an amplification at human chromosome region 4q169.81-q185.239 (marker B), comprising determining by apparatus a copy number for marker D3, marker D11, marker D26, marker D31, marker D57, marker D58, marker A1, marker A73, or marker B, thereby producing information indicative of whether human cell has a deletion at marker D3, a deletion at marker D11, a deletion at marker D26, a deletion at marker D31, a deletion at marker D57, a deletion at marker D58, an amplification at marker A1, an amplification at marker A73, or an amplification at marker B.

In an embodiment, the process comprises determining by apparatus a copy number for marker D3, marker D11, marker D26, marker D31, marker D57, marker D58, marker A1, or marker A73.

In an embodiment, the process comprises determining the copy number for two of the markers D3, D11, D26, D31, D57, D58, A1, A73, or B, thereby producing information indicative of whether the human cell has two of the markers D3, D11, D26, D31, D57, D58, A1, A73, or B. The copy number can be determined for any combination or permutation of two of the markers. In an embodiment, the two markers are D3 and D57. In another embodiment, the two markers are D31 and D58.

In an embodiment, the process comprises determining the copy number for three of the markers D3, D11, D26, D31, D57, D58, A1, A73, or B, thereby producing information indicative of whether the human cell has three of the markers D3, D11, D26, D31, D57, D58, A1, A73, or B. The copy number can be determined for any combination or permutation of three of the markers.

In an embodiment, the process comprises determining the copy number for four of the markers D3, D11, D26, D31, D57, D58, A1, A73, or B, thereby producing information indicative of whether the human cell has four of the markers D3, D11, D26, D31, D57, D58, A1, A73, or B. The copy number can be determined for any combination or permutation of four of the markers.

In an embodiment, the process comprises determining the copy number for five of the markers D3, D11, D26, D31, D57, D58, A1, A73, or B, thereby producing information indicative of whether the human cell has five of the markers D3, D11, D26, D31, D57, D58, A1, A73, or B. The copy number can be determined for any combination or permutation of five of the markers.

In an embodiment, the process comprises determining the copy number for six of the markers D3, D11, D26, D31, D57, D58, A1, A73, or B, thereby producing information indicative of whether the human cell has six of the markers D3, D11, D26, D31, D57, D58, A1, A73, or B. The copy number can be determined for any combination or permutation of six of the markers.

In an embodiment, the process comprises determining the copy number for seven of the markers D3, D11, D26, D31, D57, D58, A1, A73, or B, thereby producing information indicative of whether the human cell has seven of the markers D3, D11, D26, D31, D57, D58, A1, A73, or B. The copy number can be determined for any combination or permutation of seven of the markers.

In an embodiment, the process comprises determining the copy number for eight of the markers D3, D11, D26, D31, D57, D58, A1, A73, or B, thereby producing information indicative of whether the human cell has eight of the markers D3, D11, D26, D31, D57, D58, A1, A73, or B. The copy number can be determined for any combination or permutation of eight of the markers.

In an embodiment, the process comprises determining the copy number for nine of the markers D3, D11, D26, D31, D57, D58, A1, A73, and B, thereby producing information indicative of whether the human cell has nine of the markers D3, D11, D26, D31, D57, D58, A1, A73, and B.

In an embodiment, the process further comprises determining a copy number for at least one additional marker selected from the group consisting of: a deletion at human chromosome region 17q35.42-q56.76 (marker D1) and a deletion at human chromosome region 17q32.010-34.215 (marker D2).

A process is provided for identifying a human subject as a candidate for trastuzumab therapy comprising:

a) determining by apparatus a copy number of human chromosome region Chr18:309355-76106388 (marker D3), human chromosome region Chr15:20444124-88087873 (marker D11), human chromosome region Chr8:2780282-31010773 (marker D26), human chromosome region Chr17:1612008-46199917 (marker D31), human chromosome region Chr18:44824169-76106388 (marker D57), human chromosome region Chr17:36157799-41605371 (marker D58), human chromosome region Chr11:5755441-5766622 (marker A1), human chromosome region Chr11:5755441-5756473 (marker A73) or human chromosome region 4q169.81-q185.239 (marker B) in a cancer cell of the subject; and b) identifying the subject as a candidate for trastuzumab therapy if the copy number data of step a) is indicative of a deletion at marker D3, a deletion at marker D11, a deletion at marker D26, a deletion at marker D31, a deletion at marker D57, a deletion at marker D58, an amplification at marker A1, an amplification at marker A73, or an amplification at marker B.

An embodiment of the process comprises determining by apparatus the copy number of marker D3, marker D11, marker D26, marker D31, marker D57, marker D58, marker A1, or marker A73.

An embodiment of the process comprises determining by apparatus the copy number of two of the markers D3, D11, D26, D31, D57, D58, A1, A73, or B, and identifying the subject as a candidate for trastuzumab therapy if the copy number data of the two markers is indicative of the subject's sensitivity to trastuzumab therapy. The copy number can be determined for any combination or permutation of two of the markers. In an embodiment, the two markers are D3 and D57. In another embodiment, the two markers are D31 and D58.

An embodiment of the process comprises determining by apparatus the copy number of three of the markers three of the markers D3, D11, D26, D31, D57, D58, A1, A73, or B, and identifying the subject as a candidate for trastuzumab therapy if the copy number data of the three markers is indicative of the subject's sensitivity to trastuzumab therapy. The copy number can be determined for any combination or permutation of three of the markers.

An embodiment of the process comprises determining by apparatus the copy number of four of the markers D3, D11, D26, D31, D57, D58, A1, A73, or B, and identifying the subject as a candidate for trastuzumab therapy if the copy number data of the four markers is indicative of the subject's sensitivity to trastuzumab therapy. The copy number can be determined for any combination or permutation of four markers.

An embodiment of the process comprises determining by apparatus the copy number of five of the markers D3, D11, D26, D31, D57, D58, A1, A73, or B, and identifying the subject as a candidate for trastuzumab therapy if the copy number data of the five markers is indicative of the subject's sensitivity to trastuzumab therapy. The copy number can be determined for any combination or permutation of five markers.

An embodiment of the process comprises determining by apparatus the copy number of six of the markers D3, D11, D26, D31, D57, D58, A1, A73, or B, and identifying the subject as a candidate for trastuzumab therapy if the copy number data of the six markers is indicative of the subject's sensitivity to trastuzumab therapy. The copy number can be determined for any combination or permutation of six markers.

An embodiment of the process comprises determining by apparatus the copy number of seven of the markers D3, D11, D26, D31, D57, D58, A1, A73, or B, and identifying the subject as a candidate for trastuzumab therapy if the copy number data of the seven markers is indicative of the subject's sensitivity to trastuzumab therapy. The copy number can be determined for any combination or permutation of seven markers.

An embodiment of the process comprises determining by apparatus the copy number of eight of the markers D3, D11, D26, D31, D57, D58, A1, A73, or B, and identifying the subject as a candidate for trastuzumab therapy if the copy number data of the eight markers is indicative of the subject's sensitivity to trastuzumab therapy. The copy number can be determined for any combination or permutation of eight markers.

An embodiment of the process comprises determining by apparatus the copy number of all nine of the markers D3, D11, D26, D31, D57, D58, A1, A73, or B, and identifying the subject as a candidate for trastuzumab therapy if the copy number data of the nine markers is indicative of the subject's sensitivity to trastuzumab therapy.

An embodiment of the process further comprises determining by apparatus a copy number of one or both of human chromosome region 17q35.42-q56.76 (marker D1) and human chromosome region 17q32.010-34.215 (marker D2), wherein a deletion at marker D1 is indicative of the subject's sensitivity to trastuzumab therapy, and wherein a deletion at marker D2 is indicative of the subject's sensitivity to trastuzumab therapy, and identifying the subject as a candidate for trastuzumab therapy is the copy number data of the markers is indicative of the subject's sensitivity to trastuzumab therapy.

If the copy numbers of the markers are not determined simultaneously, then the copy number of each marker can be determined in any order.

In an embodiment of the process, the human subject has cancer and is Her 2−.

In an embodiment of the process, the human subject has cancer and is Her 2+.

In an embodiment of the process, the apparatus is a hybridization based assay.

In an embodiment of the process, the detecting step of the method of the invention comprises contacting the nucleic acid sample with one or more nucleic acid probes each of which selectively binds to a target polynucleotide sequence on the chromosome region at marker D3, marker D11, marker D26, marker D31, marker D57, marker D58, marker A1, marker A73, or marker B, under conditions in which the probe forms a stable hybridization complex with the target polynucleotide sequence; and detecting the hybridization complex. In a particular embodiment, the nucleic acid probes used in the method of the present invention are labeled with a fluorophore. In a particular embodiment, the step of detecting the hybridization complex comprises determining the copy number of the target polynucleotide sequence, thereby determining a deletion at marker D3, a deletion at marker D11, a deletion at marker D26, a deletion at marker D31, a deletion at marker D57, a deletion at marker D58, an amplification at marker A1, and amplification at marker A73, or an amplification at marker B.

A process is provided of producing information indicative of whether a human cell has a deletion at chromosome region 17q35.42-q56.76, a deletion at human chromosome region 17q32.010-q32.34.215 or an amplification at human chromosome region 4q169.81-q185.239, comprising determining by apparatus a copy number for 17q35.42-q56.76, 17q32.010-q32.34.215 or 4q169.81-q185.239, thereby producing information indicative of whether human cell has a deletion at 17q35.42-q56.76, a deletion at human 17q32.010-q32.34.215 or an amplification at 4q169.81-q185.239.

In an embodiment, the instant process comprises determining the copy number for two of 17q35.42-q56.76, 17q32.010-q32.34.215 or 4q169.81-q185.239, thereby producing information indicative of whether the human cell has two of the 17q35.42-q56.76, 17q32.010-q32.34.215 or 4q169.81-q185.239.

In an embodiment, the instant process comprises determining the copy number for all three of 17q35.42-q56.76, 17q32.010-q32.34.215 and B, thereby producing information indicative of whether the human cell has all three of 17q35.42-q56.76, 17q32.010-q32.34.215 and 4q169.81-q185.239.

A process is provided for identifying a human subject as a candidate for trastuzumab therapy comprising:
  determining by apparatus a copy number of human chromosome region 17q35.42-q56.76, human chromosome region 17q32.010-q32.34.215 or human chromosome region 4q169.81-q185.239 in a cancer cell of the subject; and
  identifying the subject as a candidate for trastuzumab therapy if the copy number data of step a) is indicative of a deletion at 17q35.42-q56.76, a deletion at 17q32.010-q32.34.215 or an amplification at 4q169.81-q185.239.

An embodiment of the process comprises determining by apparatus the copy number of two of 17q35.42-q56.76, 17q32.010-q32.34.215 or 4q169.81-q185.239, and identifying the subject as a candidate for trastuzumab therapy if the copy number data of the two markers is indicative of the subject's sensitivity to trastuzumab therapy. The copy number can be determined for any combination or permutation of two of the three markers, including but not limited to 17q35.42-q56.76/17q32.010-q32.34.215, 17q35.42-q56.76/4q169.81-q185.239 or 17q32.010-q32.34.215/4q169.81-q185.239.

In another embodiment, the process comprises determining by apparatus the copy number of all three of 17q35.42-q56.76, 17q32.010-q32.34.215 or 4q169.81-q185.239, and identifying the subject as a candidate for trastuzumab therapy if the copy number data of the three markers is indicative of the subject's sensitivity to trastuzumab therapy.

If the copy numbers of the markers are not determined simultaneously, then the copy number of each marker can be determined in any order.

In an embodiment of the process, the human subject has cancer and is Her 2−.

In an embodiment of the process, the human subject has cancer and is Her 2+.

In an embodiment of the process, the apparatus is a hybridization-based assay.

In an embodiment of the process, the detecting step of the method of the invention comprises contacting the nucleic acid sample with one or more nucleic acid probes each of which selectively binds to a target polynucleotide sequence on the chromosome region at 17q35.42-q56.76, 17q32.010-q32.34.215 or 4q169.81-q185.239, under conditions in which the probe forms a stable hybridization complex with the target polynucleotide sequence; and detecting the hybridization complex. In a particular embodiment, the nucleic acid probes used in the method of the present invention are labeled with a fluorophore. In a particular embodiment, the step of detecting the hybridization complex comprises determining the copy number of the target polynucleotide sequence, thereby determining a deletion of 17q35.42-q56.76, a deletion of marker 17q32.010-q32.34.215 or an amplification of 4q169.81-q185.239.

In an embodiment, said apparatus is selected from the group consisting of Southern blot, LOH (loss of heterozygosity), PCR, in situ hybridization (ISH) fluorescence ISH (FISH) and comparative genomic hybridization (CGH). In another embodiment, the apparatus is a comparative genomic hybridization apparatus.

In an embodiment, once the sample has been obtained and the total DNA has been extracted, genome-wide analysis of DNA copy number changes by comparative genomic hybridization (CGH) is carried out. In general, for a typical CGH measurement, total genomic DNA is isolated from test and reference cell populations, differentially labeled and hybridized to a representation of the genome that allows the binding of sequences at different genomic locations to be distinguished. Methods describing representations of genomes are described in U.S. Pat. No. 7,531,307 B2, issued May 12, 2009, Use of representations for DNA genetic analysis, the disclosure of which is incorporated by reference. Hybridization reactions can be performed under conditions of different stringency. The stringency of a hybridization reaction includes the difficulty with which any two nucleic acid molecules will hybridize to one another. For any hybridization, stringency can be varied by manipulation of three factors: temperature, salt concentration, and formamide concentration. High temperature and low salt increases stringency. Formamide decreases melting point of DNA, thus lowering the temperature at which a hybrid between two nucleic acid molecules forms. Preferably, each hybridizing polynucleotide hybridizes to its corresponding polynucleotide under reduced stringency conditions, more preferably stringent conditions, and most preferably highly stringent conditions.

The amount of specimen DNA is frequently a constraint on CGH measurements. Typical array CGH procedures use 300 ng to 3 ug of specimen DNA in the labeling reaction, equivalent to approximately 50,000 to 500,000 mammalian cells. Usually, random primer labeling protocols are employed, which also amplifies the DNA, so that several micrograms are used in the hybridization.

Array CGH has been implemented using a wide variety of techniques. On example of a genome-wide method is described in WO/2008/016374, published Feb. 7, 2008, Methods For Assessing Probabilistic Measures Of Clinical Outcome Using Genomic Profiling, the disclosure of which is incorporated herein by reference. In an embodiment, array CGH is carried out using arrays from large-insert genomic clones such as bacterial artificial chromosomes (BACs). The general principles and conditions for detection of nucleic acids, such as using array CGH (comparative genomic hybridization (CGH) to BAC microarrays), are well known for the skilled person in the art. This technique allows scanning the entire genome for DNA copy number changes therefore allowing quantitative detection of DNA copy number variation in tumor genomes with high resolution (Pinkel D, et al. High resolution analysis of DNA copy number variation using comparative genomic hybridization to microarrays. *Nat Genet* 1998; 20(2):207-11; Hodgson G, et al. Genome scanning with array CGH delineates regional alterations in mouse islet carcinomas. *Nat Genet* 2001;

29(4):459-64; and Solinas-Toldo S. et al. Matrix-based comparative genomic hybridization: biochips to screen for genomic imbalances. *Genes Chromosomes Cancer.* 1997 December; 20(4):399-407 are herein incorporated by reference).

The major technical challenge of array CGH is generating hybridization signals that are sufficiently intense and specific so that copy number changes can be detected. The signal intensity on an array element is affected by a number of factors including the base composition, the proportion of repetitive sequence content, and the amount of DNA in the array element available for hybridization.

Array elements made from genomic BAC clones typically provide more intense signals than elements employing shorter sequences such as cDNAs, PCR products, and oligonucleotides. The higher signals form the more complex array elements result in better measurement precision, allowing detection of single-copy transition boundaries even in specimens with a high proportion of normal cells.

In an embodiment, the apparatus is representational oligonucleotide microarray analysis (RONA). ROMA has an increased resolution over standard CGH and is more fully described in US 2007-0207481 A1, Sep. 6, 2007, Use of ROMA for characterizing genomic rearrangements; Lucito R et al. Representational oligonucleotide microarray analysis: a high-resolution method to detect genome copy number variation. Genome Res. 2003 October; 13(10):2291-305; and Hicks et al. Novel patterns of genome rearrangement and their association with survival in breast cancer. Genome Res. 2006 December; 16(12):1465-79, the disclosures of which are incorporated herein by reference.

In an alternative embodiment of the instant methods, the apparatus is fluorescent in situ hybridization (FISH) apparatus.

FISH is a cytogenetic technique used to detect and localize the presence or absence of specific DNA sequences on chromosomes. FISH uses fluorescent probes that bind to only those parts of the chromosome with which they show a high degree of sequence similarity. As "probe" is understood any ribopolynucleotide or desoxiribopolynucleotide sequence that specifically binds to only those parts of the chromosome with which they show a high degree of sequence similarity. The probe must be large enough to hybridize specifically with its target but not so large as to impede the hybridization process.

Many different FISH probes can be used in the present invention without limitation, e.g. probes derived from bacterial artificial chromosomes (BACs). Tiling Oligonucleotide Probes (TOPs), etc. The design of FISH probes is well know for a person skilled in the art (Bayani J, Squire J A. Curr Protoc Cell Biol. 2004 September; Chapter 22:Unit 22.4; Bayani J, Squire J. Curr Protoc Cell Biol. 2004 October; Chapter 22:Unit 22.5.; Navin, N. et al. Bioinformatics, Volume 22. Number 19, 1 Oct. 2006, pp. 2437-2438 (2)) Publisher: Oxford University Press).

The probe can be tagged directly with fluorophores, with targets for antibodies, or with biotin. Tagging can be done in various ways, such as nick translation, or PCR using tagged nucleotides.

The sample can be fixed and paraffin embedded. Thus, an additional step of deparaffination may be performed.

For hybridization, an interphase or metaphase chromosome preparation may be produced. The chromosomes are firmly attached to a substrate, usually glass. Repetitive DNA sequences must be blocked by adding short fragments of DNA to the sample. The probe is then applied to the chromosome DNA and incubated for approximately 12 hours while hybridizing. Several wash steps remove all unhybridized or partially-hybridized probes. After standard post hybridization washes the slides are stained with the DNA staining probe such DAPI and mounted with a mounting agent such as antifade. The present invention is not limited by these examples and any DNA staining probe and/or mounting agent readily known to those of skill in the art may be used.

The results are then visualized and quantified using a microscope that is capable of exciting the dye and recording images. If the fluorescent signal is weak, amplification of the signal may be necessary in order to exceed the detection threshold of the microscope. Fluorescent signal strength depends on many factors such as probe labeling efficiency, the type of probe, and the type of dye. Fluorescently-tagged antibodies or streptavidin are bound to the dye molecule. These secondary components are selected so that they have a strong signal. In an embodiment, prior to imaging all slides are evaluated by a pathologist and regions of interest are identified based on histopathologic and quality criteria including, without excluding others, tumor content, appropriate fixation, necrosis and vascularity.

The term "sample" has been previously defined and can be applied to any type of biological sample from a patient, such as a biopsy sample, tissue, cell or fluid (serum, saliva, semen, sputum, cerebral spinal fluid (CSF), tears, mucus, sweat, milk, brain extracts and the like). In a particular embodiment, said sample is a tumour tissue sample or portion thereof. In a more particular embodiment, said tumor tissue sample is a breast tumor tissue sample from a patient suffering from breast cancer or a formalin embedded breast tissue sample.

In a particular embodiment of the instant methods, determining if the copy number is indicative of a deletion at marker D3, a deletion at marker D11, a deletion at marker D26, a deletion at marker D31, a deletion at marker D57, a deletion at marker D58, an amplification at marker A1, an amplification at marker A73, and/or an amplification at marker B, comprises comparing the copy number of the selected marker or markers to the copy number of a diploid reference. Copy number can then be defined as the ratio of hybridization signal at any locus in the genome comparing a tumor DNA sample to a DNA sample from the standard diploid reference.

A method is provided of treating a human subject afflicted with cancer comprising:
obtaining information indicative of whether the human subject is a candidate for trastuzumab therapy, the information based on
a copy number of human chromosome region Chr18: 309355-76106388 (marker D3), human chromosome region Chr15:20444124-88087873 (marker D11), human chromosome region Chr8:2780282-31010773 (marker D26), human chromosome region Chr17: 1612008-46199917 (marker D31), human chromosome region Chr18:44824169-76106388 (marker D57), human chromosome region Chr17:36157799-41605371 (marker D58), human chromosome region Chr11:5755441-5766622 (marker A1), human chromosome region Chr11:5755441-5756473 (marker A73) or human chromosome region 4q169.81-q185.239 (marker B), wherein the subject is a candidate for trastuzumab therapy if the copy number data is indicative of a deletion at marker D3, a deletion at marker D11, a deletion at marker D26, a deletion at marker D31, a deletion at marker D57, a deletion at marker D58, an amplification at marker A1, an amplification at marker A73, or an amplification at marker B; and if the information indicates that the human subject is a candidate for trastuzumab therapy, then administering to the human subject an amount of trastuzumab effective to treat the human subject afflicted with cancer.

In an embodiment of the method the information is based on copy number of marker D3, marker D11, marker D26, marker D31, marker D57, marker D58, marker A1, or marker A73.

In an embodiment of the method, the information is based on a copy number of two of the markers D3, D11, D26, D31, D57, D58, A1, A73, or B, the copy number data of the two markers being indicative of the subject's sensitivity to trastuzumab therapy. The copy number can be determined for any combination or permutation of two of the markers. In an embodiment, the two markers are D3 and D57. In another embodiment, the two markers are D31 and D58.

In an embodiment of the method, the information is based on a copy number of three of the markers D3, D11, D26, D31, D57, D58, A1, A73, or B, the copy number data of the three markers being indicative of the subject's sensitivity to trastuzumab therapy. The copy number can be determined for any combination or permutation of three markers.

In an embodiment of the method, the information is based on a copy number of four of the markers D3, D11, D26, D31, D57, D58, A1, A73, or B, the copy number data of the four markers being indicative of the subject's sensitivity to trastuzumab therapy. The copy number can be determined for any combination or permutation of four markers.

In an embodiment of the method, the information is based on a copy number of five of the markers D3, D11, D26, D31, D57, D58, A1, A73, or B, the copy number data of the five markers being indicative of the subject's sensitivity to trastuzumab therapy. The copy number can be determined for any combination or permutation of five markers.

In an embodiment of the method, the information is based on a copy number of six of the markers D3, D11, D26, D31, D57, D58, A1, A73, or B, the copy number data of the six markers being indicative of the subject's sensitivity to trastuzumab therapy. The copy number can be determined for any combination or permutation of six markers.

In an embodiment of the method, the information is based on a copy number of seven of the markers D3, D11, D26, D31, D57, D58, A1, A73, or B, the copy number data of the seven markers being indicative of the subject's sensitivity to trastuzumab therapy. The copy number can be determined for any combination or permutation of seven markers.

In an embodiment of the method, the information is based on a copy number of eight of the markers D3, D11, D26, D31, D57, D58, A1, A73, or B, the copy number data of the eight markers being indicative of the subject's sensitivity to trastuzumab therapy. The copy number can be determined for any combination or permutation of eight markers.

In an embodiment of the method, the information is based on a copy number of all nine of the markers D3, D11, D26, D31, D57, D58, A1, A73, and B, the copy number data of the nine markers being indicative of the subject's sensitivity to trastuzumab therapy.

An embodiment of the method further comprises obtaining additional information indicative of whether the human subject is a candidate for trastuzumab therapy based on a copy number of one or both of human chromosome region 17q35.42-q56.76 (marker D1) and human chromosome region 17q32.010-34.215 (marker D2), wherein the subject is a candidate for trastuzumab therapy if the copy number is indicative of a deletion at one or both of marker D1 and marker D2.

In a particular embodiment of the instant methods, determining if the copy number is indicative of a deletion of 17q35.42-q56.76, a deletion of 17q32.010-q32.34.215, and/or an amplification of 4q169.81-q185.239 comprises comparing the copy number of the selected marker or markers to the copy number of a diploid reference. Copy number can then be defined as the ratio of hybridization signal at any locus in the genome comparing a tumor DNA sample to a DNA sample from the standard diploid reference.

A method is provided of treating a human subject afflicted with cancer comprising:

a) obtaining information indicative of whether the human subject is a candidate for trastuzumab therapy, the information based on a copy number of human chromosome region 17q35.42-q56.76, human chromosome region 17q32.010-q32.34.215 or human chromosome region 4q169.81-q185.239, wherein the subject is a candidate for trastuzumab therapy if the copy number data is indicative of a deletion at 17q35.42-q56.76, a deletion at 17q32.010-q32.34.215 or an amplification at 4q169.81-q185.239; and b) if the information indicates that the human subject is a candidate for trastuzumab therapy, then administering to the human subject an amount of trastuzumab effective to treat the human subject afflicted with cancer.

In an embodiment of the method, the information is based on a copy number of two of 17q35.42-q56.76, 17q32.010-q32.34.215 or 4q169.81-q185.239, the copy number data of the two markers being indicative of the subject's sensitivity to trastuzumab therapy. The copy number can be determined for any combination or permutation of two of the three markers, including but not limited to 17q35.42-q56.76/17q32.010-q32.34.215, 17q35.42-q56.76/4q169.81-q185.239 or 17q32.010-q32.34.215/4q169.81-q185.239.

In an embodiment of the method, the information is based on a copy number of all three of 17q35.42-q56.76, 17q32.010-q32.34.215 and 4q169.81-q185.239, the copy number data of the three markers being indicative of the subject's sensitivity to trastuzumab therapy.

In an embodiment, the subject is Her2−. In an embodiment, the subject is Her2+.

The methods provided herein to identify a subject as a candidate for trastuzumab therapy can also be used to determine the sensitivity of a subject to trastuzumab therapy and/or predict the responsiveness of a subject to trastuzumab therapy, wherein the subject has cancer.

If the copy numbers of the markers are not determined simultaneously, then the copy number of each marker can be determined in any order.

In a particular embodiment, the subject has breast cancer. In another embodiment, the subject has breast cancer cells. In other embodiments, the candidate subject has been previously diagnosed as having cancer cells from diseases including, but not limited to, leukemia, brain cancer, kidney cancer, lymphoma, eye cancer, connective tissue cancer, Hodgkin's disease, bone cancer, testicular cancer, cervical cancer, thyroid cancer, melanoma, skin cancer, uterine cancer, lung cancer, colon cancer, rectal cancer, ovarian cancer, bladder cancer, larynx cancer, prostate cancer, stomach cancer, breast cancer, and pancreatic cancer. In another embodiment the subject has a cancer affected by changes in the Human Epidermal growth factor Receptor 2 (Her2) pathway.

In an embodiment, trastuzumab therapy is administered as a monotherapy. In another embodiment, trastuzumab therapy is administered as an adjuvant therapy.

In order to carry out the invention, a sample is obtained from the subject under study. In a particular embodiment, said sample is a tumour tissue sample or portion thereof. In a more particular embodiment, said tumor tissue sample is a breast tumor tissue sample from a patient suffering from breast cancer. Said sample can be obtained by conventional methods, e.g., biopsy, by using methods well known to those of ordinary skill in the related medical arts. Methods for obtaining the sample from the biopsy include gross apportioning of a mass, or microdissection or other art-known cell-separation methods. Tumour cells can additionally be obtained from fine needle aspiration cytology.

Samples can be obtained from subjects previously diagnosed or not diagnosed with breast cancer, or from subjects who are receiving or have previously received anti-breast cancer treatment. In a particular embodiment, samples can be obtained from patients who have not previously received any anti-breast cancer treatment.

In order to simplify conservation and handling of the samples, these can be formalin-fixed and paraffin-embedded or first frozen and then embedded in a cryosolidifiable medium, such as OCT-Compound, through immersion in a highly cryogenic medium that allows for rapid freeze.

In a particular embodiment, the copy number of a marker, including but not limited to D3, D11, D26, D31, D57, D58, A1, A73, B, D1, D2, or Her2, is determined using nucleic acids obtained from fresh tissue from a biopsy or fine needle aspiration cytology.

Fixed and paraffin-embedded tissue samples are broadly used storable or archival tissue samples in the field of oncology. Nucleic acid may be isolated from an archival pathological sample or biopsy sample which is first deparaffinized.

An exemplary deparaffinization method involves washing the paraffinized sample with an organic solvent, such as xylene, for example. Deparaffinized samples can be rehydrated with an aqueous solution of a lower alcohol. Suitable lower alcohols, include, for example, methanol, ethanol, propanols, and butanols. Deparaffinized samples may be rehydrated with successive washes with lower alcoholic solutions of decreasing concentration, for example. Alternatively, the sample may be simultaneously deparaffinized and rehydrated. The sample is then lysed and nucleic acid is extracted from the sample. As an illustrative, non limitative example, tissue selected for fixation and paraffin embedding can be fixed in 10% buffered formalin for 16 hours to 48 hours. After this period of time, said tissue will be embedded in paraffin following conventional techniques. Nevertheless, nucleic acid quality issues are especially delicate when analyzing formalin-fixed tissue samples.

In a particular embodiment, the copy number of a marker, including but not limited to D3, D11, D26, D31, D57, D58, A1, A73, B, D1, D2, or Her2, is determined using nucleic acids obtained from a biopsy tissue sample or fine needle aspiration cytology. Because of the variability of the cell types in diseased-tissue biopsy material, and the variability in sensitivity of the diagnostic methods used, the sample size required for analysis may range from 1, 10, 50, 100, 200, 300, 500, 1,000, 5,000, 10.000, to 50,000 or more cells. The appropriate sample size may be determined based on the cellular composition and condition of the biopsy or cytology, and the standard preparative steps for this determination and subsequent isolation of the nucleic acid for use in the invention are well known to one of ordinary skill in the art.

Using standard methods, the biological sample may be treated to physically or mechanically disrupt tissue or cell structure, to release intracellular components into an aqueous or organic solution to prepare nucleic acids for further analysis. The nucleic acids may be extracted from the sample by procedures known to the skilled person and commercially available. In a particular embodiment, the total DNA extracted from tissue samples represents the working material suitable for subsequent detection of the genetic marker of interest. Once the sample has been obtained and the total DNA has been extracted, amplification of nucleic acid may be carried out in order to produce sufficient sample material for further detection procedures. Several techniques can be used for producing sufficient starting material. These techniques include polymerase chain reaction (PCR), degenerate primer PCR using one or several sets of primers, rolling circle amplification, etc. Examples of techniques sufficient to direct persons of skill through in vitro amplification methods are found in Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for isolation of nucleic acids from FFPE tissues and for genomic PCR amplification are known in the art. See, e.g., RecoverAll™ Total Nucleic Acid Isolation Kit for FPPE (Ambion) and WGA1 GenomePlex® Whole Genome Amplification Kit (Sigma).

In a particular embodiment, the amplification of the DNA is carried out by means of PCR. The general principles and conditions for amplification and detection of nucleic acids, such as using PCR, are well known for the skilled person in the art.

The instant invention provides a kit for identifying a subject's sensitivity to trastuzumab therapy, said kit comprising one or more nucleic acid probes each of which selectively bind to a target polynucleotide sequence of the chromosome region comprising one of human chromosome region Chr18:309355-76106388 (marker D3), human chromosome region Chr15:20444124-88087873 (marker D11), human chromosome region Chr8:2780282-31010773 (marker D26), human chromosome region Chr17:1612008-46199917 (marker D31), human chromosome region Chr18:44824169-76106388 (marker D57), human chromosome region Chr17:36157799-41605371 (marker D58), human chromosome region Chr11:5755441-5766622 (marker A1), human chromosome region Chr11:5755441-5756473 (marker A73) or human chromosome region 4q169.81-q185.239 (marker B) under conditions in which the probe forms a stable hybridization complex with the target polynucleotide sequence. An embodiment of the kit contains one or more nucleic acid probes which selectively bind to target polynucleotide sequences of the chromosome regions comprising two of markers D3, D31, D57, D58, or B.

In an embodiment, the kit contains one or more nucleic acid probes each of which selectively bind to a target polynucleotide sequence of the chromosome region comprising one of markers D3, D11, D26, D31, D57, D58, A1, or A73.

An embodiment of the kit contains one or more nucleic acid probes which selectively bind to target polynucleotide sequences of the chromosome regions comprising two of markers D3, D11, D26, D31, D57, D58, A1, A73, or B.

An embodiment of the kit contains one or more nucleic acid probes which selectively bind to target polynucleotide sequences of the chromosome regions comprising three of markers D3, D11, D26, D31, D57, D58, A1, A73, or B.

An embodiment of the kit contains one or more nucleic acid probes which selectively bind to target polynucleotide sequences of the chromosome regions comprising four of markers D3, D11, D26, D31, D57, D58, A1, A73, or B.

An embodiment of the kit contains one or more nucleic acid probes which selectively bind to target polynucleotide sequences of the chromosome regions comprising five of markers D3, D11, D26, D31, D57, D58, A1, A73, or B.

An embodiment of the kit contains one or more nucleic acid probes which selectively bind to target polynucleotide sequences of the chromosome regions comprising six of markers D3, D11, D26, D31, D57, D58, A1, A73, or B.

An embodiment of the kit contains one or more nucleic acid probes which selectively bind to target polynucleotide sequences of the chromosome regions comprising seven of markers D3, D11, D26, D31, D57, D58, A1, A73, or B.

An embodiment of the kit contains one or more nucleic acid probes which selectively bind to target polynucleotide sequences of the chromosome regions comprising eight of markers D3, D11, D26, D31, D57, D58, A1, A73, or B.

An embodiment of the kit contains one or more nucleic acid probes which selectively bind to target polynucleotide sequences of the chromosome regions comprising nine of markers D3, D11, D26, D31, D57, D58, A1, A73, and B.

An embodiment of the kit further comprises one or more nucleic acid probes each of which selectively bind to a target polynucleotide sequence of a chromosome region selected from the group consisting of: human chromosome region 17q35.42-q56.76 (marker D1) and human chromosome region 17q32.010-34.215 (marker D2).

An embodiment of the kit further comprises one or more nucleic acid probes which selectively bind to a target polynucleotide sequence of the chromosome region comprising Her2/neu.

Probes can be obtained from commercial sources or they can be made non-commercially using well known techniques. A technique to design probes is disclosed in US 2005-0032095 A1, published Feb. 10, 2005, Virtual representations of nucleotide sequences, the disclosure of which is incorporated by reference. Sources of DNA for use in constructing DNA probes include genomic DNA, cloned DNA sequences such as bacterial artificial chromosomes (BAC), somatic cell hybrids that contain one or a part of a human chromosome along with the normal chromosome complement of the host, and chromosomes purified by flow cytometry or microdissection. The region of interest can be isolated through cloning or by site-specific amplification via the polymerase chain reaction (PCR). See, for example, Nath, et al., Biotechnic Histochem, 1998, 73 (1): 6-22; Wheeless. et al., Cytometry, 1994, 17:319-327; and U.S. Pat. No. 5,491,224. Synthesized oligomeric DNA or PNA probes can also be used.

The size of the chromosomal region detected by the probes used in the invention can vary. For locus-specific probes that are directly labeled, probes of at least 100,000 bases in complexity may be used, and unlabeled blocking nucleic acid may be used, as disclosed in U.S. Pat. No. 5,756,696, herein incorporated by reference, to avoid non-specific binding of the probe. It is also possible to use unlabeled, synthesized oligomeric nucleic acid or protein nucleic acid as the blocking nucleic acid. For targeting a particular gene locus, the probes may span approximately the entire genomic coding locus of the gene.

Chromosomal probes can contain any detection moiety that facilitates the detection of the probe when hybridized to a chromosome. Effective detection moieties include both direct and indirect labels as described below. An embodiment of the instant kit contains a nucleic acid probe or probes which are directly labeled. An embodiment of the instant kit contains a nucleic acid probe or probes which are indirectly labeled.

Chromosomal probes can be directly labeled with a detectable label. Examples of detectable labels include fluorophores (i.e., organic molecules that fluoresce after absorbing light), radioactive isotopes (e.g., 32p, and 3H) and chromophores (e.g., enzymatic markers that produce a visually detectable marker). Fluorophores are preferred and can be directly labeled following covalent attachment to a nucleotide by incorporating the labeled nucleotide into the probe with standard techniques such as nick translation, random priming, and PCR labeling. Alternatively, deoxycytidine nucleotides within the probe can be transaminated with a linker. The fluorophore can then be covalently attached to the transaminated deoxycytidine nucleotides. See, e.g., U.S. Pat. No. 5,491,224 to Bittner, et al., which is incorporated herein by reference. Useful probe labeling techniques are described in Molecular Cytogenetics: Protocols and Applications, Y.-S. Fan, Ed., Chap. 2, "Labeling Fluorescence In Situ Hybridization Probes for Genomic Targets", L. Morrison et. al., p. 21-40, Humana Press, © 2002 (hereafter cited as "Morrison 2002"), incorporated herein by reference.

Examples of fluorophores that can be used in the methods described herein are: 7-amino-4-methylcoumarin-3-acetic acid (AMCA), Texas Red™ (Molecular Probes, Inc., Eugene, Oreg.); 5-(and-6)-carboxy-X-rhodamine, lissamine rhodamine B, 5-(and-6)-carboxyfluorescein; fluorescein-5-isothiocyanate (FITC); 7-diethylaminocoumarin-3-carboxylic acid, tetramethylrhodamine-5-(and-6)-isothiocyanate; 5-(and -6)-carboxytetramethylrhodamine; 7-hydroxycoumarin-3-carboxylic acid; 6-[fluorescein 5-(and-6)-carboxamido]hexanoic acid; N-(4,4-difluoro-5, 7-dimethyl-4-bora-3a,4a diaza-3-indacenepropionic acid; eosin-5-isothiocyanate; erythrosine-5-isothiocyanate; 5-(and-6)-carboxyrhodamine 6G; and Cascade™ blue acetylazide (Molecular Probes, Inc., Eugene, Oreg.).

When multiple probes are used, fluorophores of different colors can be chosen such that each chromosomal probe in the set can be distinctly visualized. Preferably the probe panel of the invention will comprise two or three separate probes, each labeled with a separate fluorophore. Use of four probes may be preferred as providing the best balance between clinical sensitivity (sensitivity can increase with added probes) and imaging/detection complexity (complexity can increase with added probes). It is also within the scope of the invention to use multiple panels sequentially on the same sample: in this embodiment, after the first panel is hybridized, the results are imaged, the sample is destained and then is hybridized with a second panel. Multiple panels may also be hybridized each to a different portion of the same specimen. e.g. to serial sections from a paraffin block of a fixed and embedded specimen.

Probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems, such as those available from MetaSystems or Applied Imaging. Alternatively, techniques such as flow cytometry can be used to examine the hybridization pattern of the chromosomal probes.

Probes can also be labeled indirectly, e.g., with biotin or digoxygenin by means well known in the art. However, secondary detection molecules or further processing are then required to visualize the labeled probes. For example, a probe labeled with biotin can be detected by avidin conjugated to a detectable marker, e.g., a fluorophore. Additionally, avidin can be conjugated to an enzymatic marker such as alkaline phosphatase or horseradish peroxidase. Such enzymatic markers can be detected in standard calorimetric reactions using a substrate for the enzyme. Substrates for alkaline phosphatase include 5-bromo-4-chloro-3-indolyl-phosphate and nitro blue tetrazolium. Diaminobenzoate can be used as a substrate for horseradish peroxidase.

The probes and probe sets useful with the methods of the invention can be packaged with other reagents into kits to be used in carrying out the methods of the invention. Useful probe sets and kits can comprise probes to Her2 and probes to one or more of markers D3, D11, D26, D31, D57, D58, A1, A73, and B. Additionally, probe sets and kits may only include a probe or probes to one or more of marker D3, D11, D26, D31, D57, D58, A1, A73, and B. Alternatively, one or more reference probes may be included in the kits already mentioned.

In a further embodiment, an array-based format can be used in which the nucleic acids or the nucleic acid probes of the invention are attached to a solid surface. In a further embodiment, the attached probe or probes comprise a nucleic acid array. In this type of format, a large number of different hybridization reactions can be run essentially "in parallel." This provides rapid, essentially simultaneous, evaluation of a large number of nucleic acid probes. Methods for immobilizing the polynucleotides on the surface and derivatizing the surface are known in the art; see, for example, U.S. Pat. No. 6,664,057, and are also described above. These arrays can be used in CGH or ROMA analysis.

In a further embodiment, the kit comprises instructional material which teaches that the detection of one or more of a deletion at marker D3, a deletion at marker D11, a deletion at marker D26, a deletion at marker D31, a deletion at marker D57, a deletion at marker D58, an amplification at marker A1, an amplification at marker A73, or an amplification at marker B indicates that a subject is likely to be sensitive to trastuzumab therapy.

In another embodiment, the invention relates to the use of a kit of the invention for identifying a subject as a candidate for trastuzumab therapy, wherein if said components of the kit detect a deletion at marker D3, a deletion at marker D11, a deletion at marker D26, a deletion at marker D31, a deletion at marker D57, a deletion at marker D58, an amplification at marker A1, an amplification at marker A73, or an amplification at marker B, then the subject will be considered a candidate for trastuzumab therapy.

The invention further provides a method of identifying a genomic marker comprising: a) obtaining a set of genomic copy number profiles; b) deriving from the set of genomic copy number profiles a set of N copy number events Aj, wherein j=1, . . . , N and wherein each copy number event is associated with a specific interval of the genome and a real number Uj, wherein $0 \leq Uj \leq 1$; c) setting Uj to 1; d) determining for each copy number event Aj and an interval I an explanation value Ej(I), wherein Ej(I)=UjL(I)/L(Aj) if I is contained in Aj and Ej(I)=0 if I is not contained in Aj, and wherein L(I) is the length of interval I and L(Aj) is the length of copy number event Aj; e) summing the values determined in step (d) for interval I to provide an explanation of the set of copy number events, E(I); f) determining an optimal explanation value S of the set of copy number events and a corresponding optimal explaining interval C, wherein S=maxIE(I) and wherein C=argmaxIE(I); g) updating Uj by subtracting the value of C determined in step (f) for all j=1, . . . , N; h) repeating step (d) through step (g) at least one time; and i) selecting an optimal explaining interval whose optimal explanation value is statistically significant, thereby identifying an optimal explaining interval as a genomic marker.

In an embodiment, the set of genomic copy number profiles are obtained from subjects afflicted with a cancer.

In an embodiment, the subjects are Her2−.

In an embodiment, the subjects are Her2+.

In an embodiment, the subjects have a cancer affected by changes in the Her2/neu pathway.

In an embodiment, the subjects have breast cancer.

In an embodiment, the genomic marker is indicative of sensitivity to trastuzumab therapy.

All publications and other references mentioned herein are incorporated by reference in their entirety, as if each individual publication or reference were specifically and individually indicated to be incorporated by reference. Publications and references cited herein are not admitted to be prior art.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

EXAMPLES

Example 1

CALGB9342

Samples of DNA were obtained from formalin-fixed paraffin-embedded (FFPE) tumor tissue samples from patients that had been enrolled in clinical trial CALGB9342. The details of the trial are described in Winer E P et al. "Failure of higher-dose paclitaxel to improve outcome in patients with metastatic breast cancer: cancer and leukemia group B trial 9342." *J Clin Oncol*. 2004 Jun. 1; 22(11): 2061-8, the disclosure of which in its entirety is hereby incorporated by reference into this application. A brief description of the study follows.

Purpose

Cancer and Leukemia Group B Protocol 9342 was initiated to determine the optimal dose of paclitaxel administered as a 3-hour infusion every 3 weeks to women with metastatic breast cancer.

Patients and Methods

Four hundred seventy-four women with metastatic breast cancer who had received one or no prior chemotherapy regimens were randomly assigned to one of three paclitaxel dosing regimens-175 mg/m$^2$, 210 mg/m$^2$, or 250 mg/m$^2$-each administered as a 3-hour infusion every 3 weeks. Women completed self-administered quality of life and symptom assessment questionnaires at baseline and after three cycles of treatment.

Results

No evidence of a significant dose-response relationship was demonstrated over the dose range assessed. Response rates were 23%, 26%, and 21% for the three regimens, respectively. A marginally significant association (P=0.04) was seen between dose and time to progression: however, in a multivariate analysis, the difference was even less apparent. No statistically significant difference was seen in survival. Neurotoxicity and hematologic toxicity were more severe on the higher dose arms. There was no significant difference in quality of life on the three arms.

Conclusion

Higher doses of paclitaxel administered as a 3-hour infusion to women with metastatic breast cancer did not improve response rate, survival, or quality of life. There was a slight improvement in time to progression with higher dose therapy, which was offset by greater toxicity. When a 3-hour infusion of paclitaxel is administered every 3 weeks, 175 mg/m$^2$ should be considered the optimal dose.

Example 2

CALGB9840

Samples of DNA were obtained from formalin-fixed paraffin-embedded (FFPE) tumor tissue samples from patients that had been enrolled in clinical trial CALGB9342. The details of the trial are described in Seidman A D et al. "Randomized phase III trial of weekly compared with every-3-weeks paclitaxel for metastatic breast cancer, with trastuzumab for all HER-2 overexpressors and random assignment to trastuzumab or not in HER-2 nonoverexpressors: final results of Cancer and Leukemia Group B protocol 9840." J Clin Oncol. 2008 Apr. 1:26(10):1642-9, the disclosure of which in its entirety is hereby incorporated by reference into this application. A brief description of the study follows.

Purpose

Phase II trials suggested that weekly paclitaxel might be more effective and less toxic than every-3-weeks administration for metastatic breast cancer (MBC). Cancer and Leukemia Group B (CALGB) protocol 9840 was initiated to address this question. Subsequently trastuzumab was demonstrated to improve outcomes of paclitaxel therapy for human epidermal growth factor receptor-2 (Her2)-positive patients, and was therefore incorporated. Because inhibition of Her-family signaling had potential efficacy even without Her2 overexpression, we randomly assigned for trastuzumab in this population.

Patients and Methods

Patients were randomly assigned to paclitaxel 175 mg/m$^2$ every 3 weeks or 80 mg/m$^2$ weekly. After the first 171 patients, all Her2-positive patients received trastuzumab; Her2 nonoverexpressors were randomly assigned for trastuzumab, in addition to paclitaxel schedule. A total of 577 patients were treated on 9840. An additional 158 patients were included in analyses, for combined sample of 735. The primary end point was response rate (RR); secondary end points were time to progression (TTP), overall survival, and toxicity. Primary comparisons were between weekly versus every-3-weeks paclitaxel, and trastuzumab versus no trastuzumab in Her2 nonoverexpressors.

Results

In the combined sample, weekly paclitaxel was superior to every-3-weeks administration: RR (42% v 29%, unadjusted odds ratio [OR]=1.75; P=0.0004), TTP (median, 9 v 5 months: adjusted HR_1.43; P<0.0001), and survival (median, 24 v 12 months; adjusted HR=1.28; P=0.0092). For Her2 nonoverexpressors, trastuzumab did not improve efficacy. Grade 3 neuropathy was more common with weekly dosing (24% v 12%; P=0.0003).

Conclusion

Weekly paclitaxel is more effective than every-3-weeks administration for NBC. Trastuzumab did not improve efficacy for Her2 nonoverexpressors. Neurotoxicity is a treatment-limiting toxicity for weekly paclitaxel.

Example 3

Materials and Methods

DNA was obtained from formalin-fixed paraffin-embedded (FPPPE) tumor tissue samples from patients that had been enrolled in clinical trials (CALGB9840 and CALGB9342). These trials were originally designed to test response to taxane chemotherapy along with response to Herceptin® (trastuzumab) therapy. DNA samples were anonymized, but associated with complete clinical information, including long term (>5 years) followup for disease progression, survival, histopathology and had been tested for Her2/neu (ERBB2) gene amplification by the clinical standard technique known as fluorescence in situ hybridization (FISH). mRNA gene expression data was also available for Her2/neu plus 700 additional genes. The sample set contained approximately equal numbers of four test categories: 1. Her2 FISH negative, untreated with Herceptin: 2. Her2 FISH positive (FISH ratio>2), untreated with Herceptin: 3. Her2 FISH negative, treated with Herceptin; 4. Her2 FISH positive, treated with Herceptin.

DNA Preparation.

DNA isolated from these samples was extracted using commercially available techniques for purifying DNA from FFPPE samples. DNA was stored frozen at −20° C.

Genome Copy Number Analysis

Whole genome copy number analysis was performed on high density microarrays supplied by Agilent (244K features) or NimbleGen (1.1 million features). Array hybridizations were performed by the two color method in comparison to a male standard for which naturally occurring copy number variations (CNV's) have been previously mapped. Intrachip normalization will be computed by a combination of LOWESS and LOCAL normalization algorithms. High density array data was resolved into discrete events (amplifications and deletions) using the KS segmenter algorithm (Hicks at al., *Genome Research,* 2006). Frequencies of events and patterns of events (e.g. Firestorm Index) will be calculated using methods described by Hicks et al (*Genome Research,* 2006). Correlations with clinical parameters were calculated using standard methods.

Statistical Analysis

Figure 2:
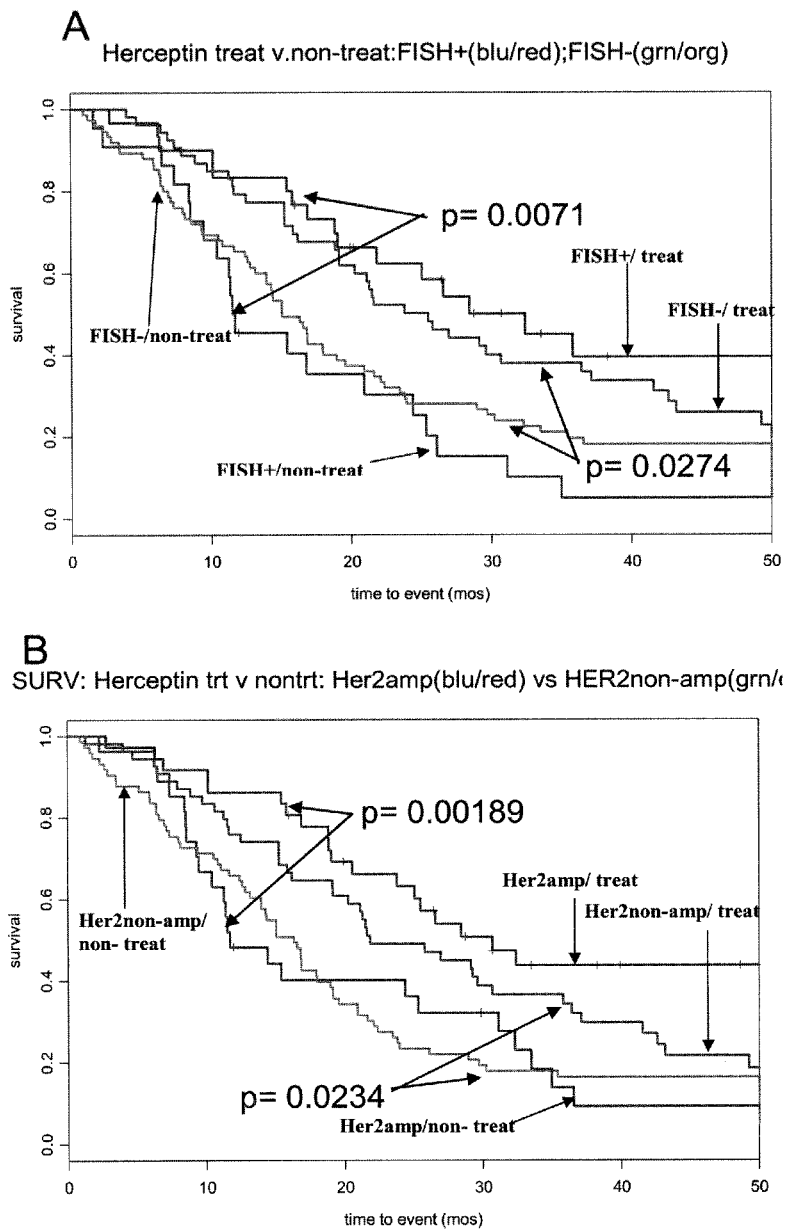
FIG. 2. Plot of trastuzumab response (treated vs. untreated) plotted as overall survival (y axis) over time in months (x axis) for patients assayed as ERBB2 amplified ("FISH+" and "HER2amp") or non-amplified ("FISH−" and "HER2non-amp") by FISH (FIG. 2A) or aCGH (FIG. 2B).
Figure 3A:
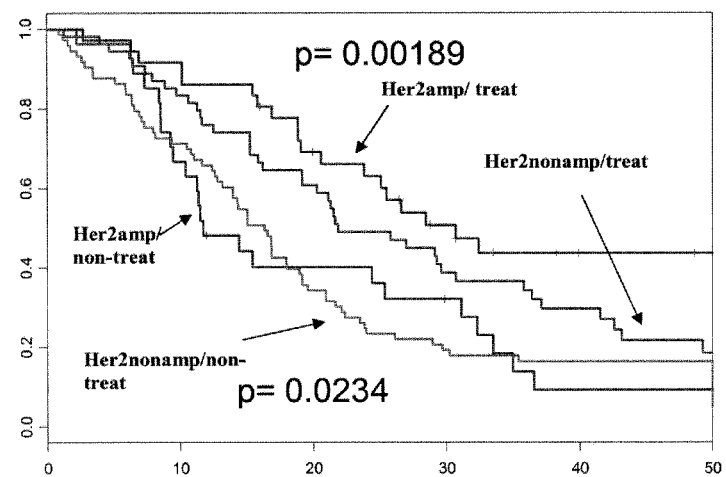
FIG. 3A. Plot of trastuzumab response measured as overall survival (treated vs. untreated) for patients assayed as positive for Her2 amplification by aCGH ("Her2amp") or negative for Her2 amplification by aCGH ("Her2nonamp").
Figure 3B:
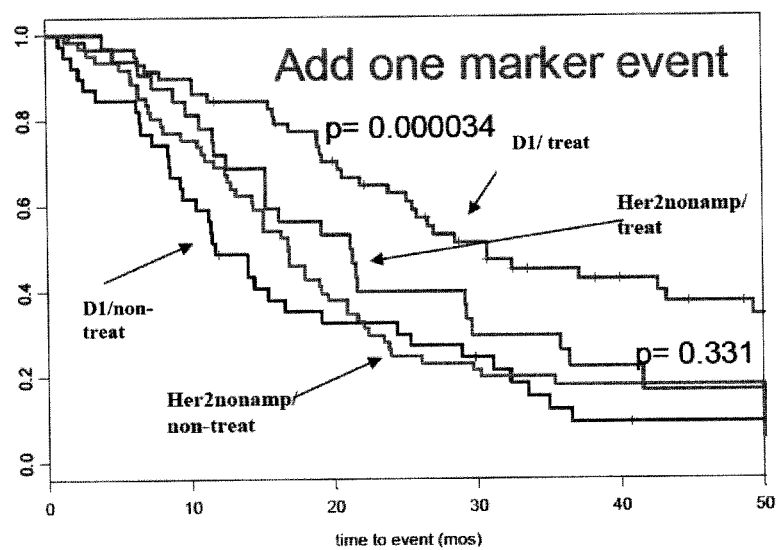
FIG. 3B. Plot of trastuzumab response measured as overall survival (treated vs. untreated) for patients assayed as positive for Her2 amplification by aCGH plus those negative for Her2 amplification but carrying a deletion at marker D1 ("D1") compared to those negative for Her2 amplification by aCGH and not carrying a deletion at marker D1 ("Her2nonamp").
Figure 3C:
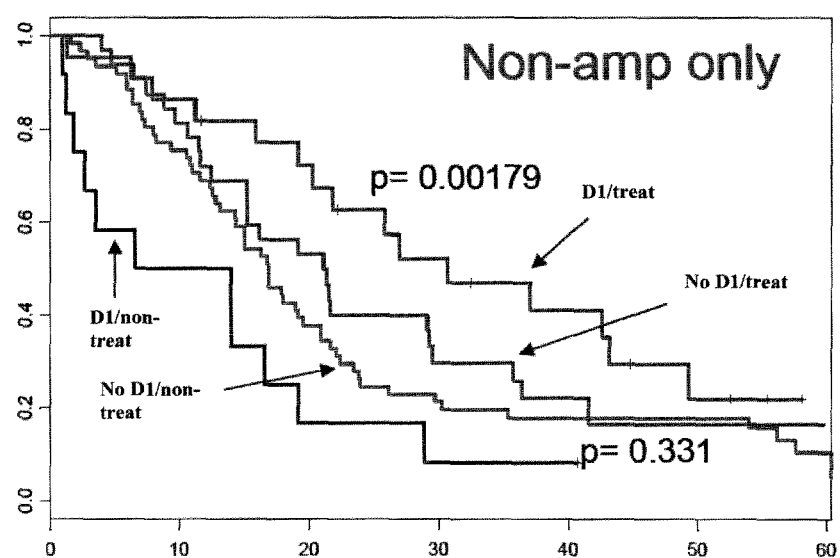
FIG. 3C. Plot of trastuzumab response measured as overall survival (treated vs. untreated) for patients assayed as negative for Her2 amplification by aCGH ("D1") and carrying a deletion at marker D1 or negative for Her2 amplification by aCGH not carrying a deletion at marker D1 ("No D1").
Figure 3D:
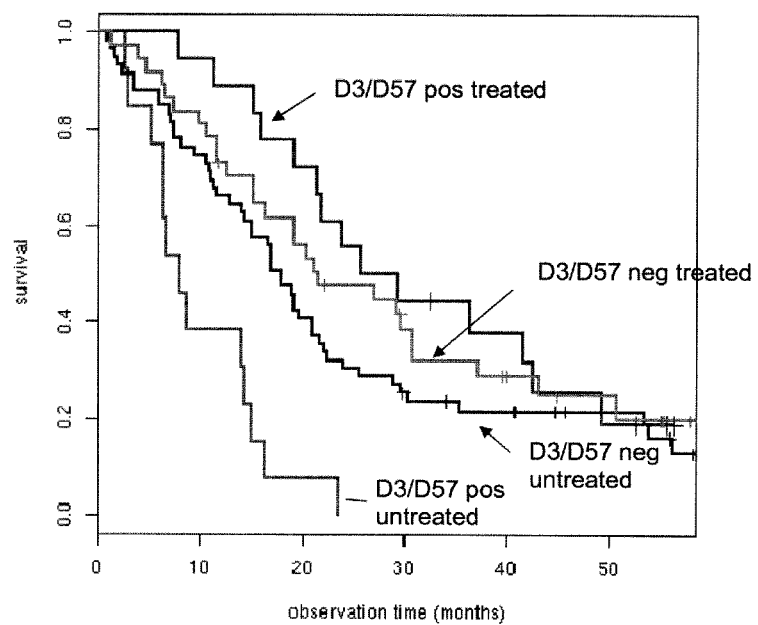
FIG. 3D. Plot of trastuzumab response measured as overall survival (treated vs. untreated) for patients assayed as negative for Her2 amplification and positive for deletions at combined marker D3/D57 compared to those negative for Her2 amplification and not carrying deletions at combined marker D3/D57.
Figure 3E:
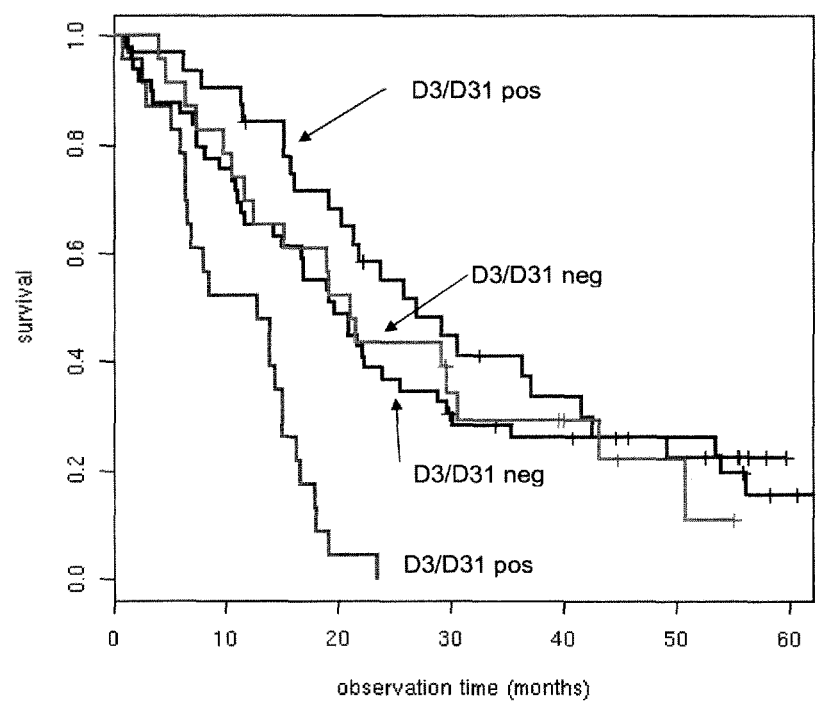
FIG. 3E. Plot of trastuzumab response measured as overall survival (treated vs. untreated) for patients assayed as negative for Her2 amplification and positive for a deletion at marker D3 or a deletion at marker D31 compared to those negative for Her2 amplification and not carrying a deletion at marker D3 or a deletion at marker D31.
Figure 3F:
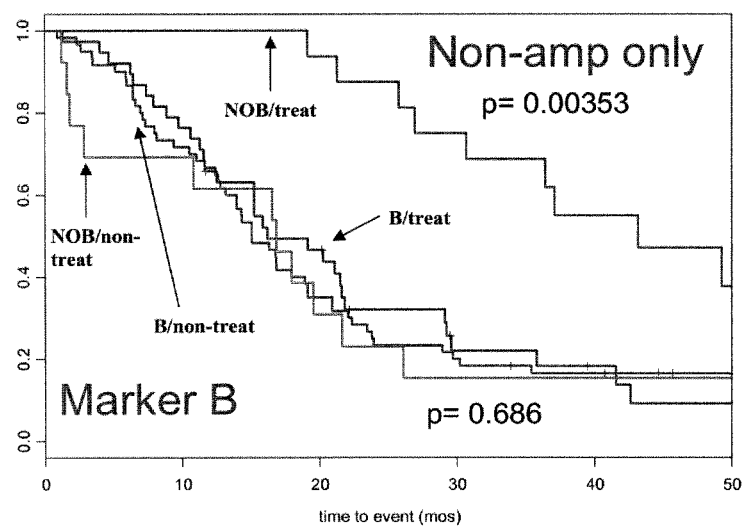
FIG. 3F. Plot of trastuzumab response measured as overall survival (treated vs. untreated) for patients assayed as negative for Her2 amplification by aCGH ("B") and carrying an amplification at marker B or negative for Her2 amplification by aCGH and not carrying an amplification at marker B ("NOB").
Figure 4A:
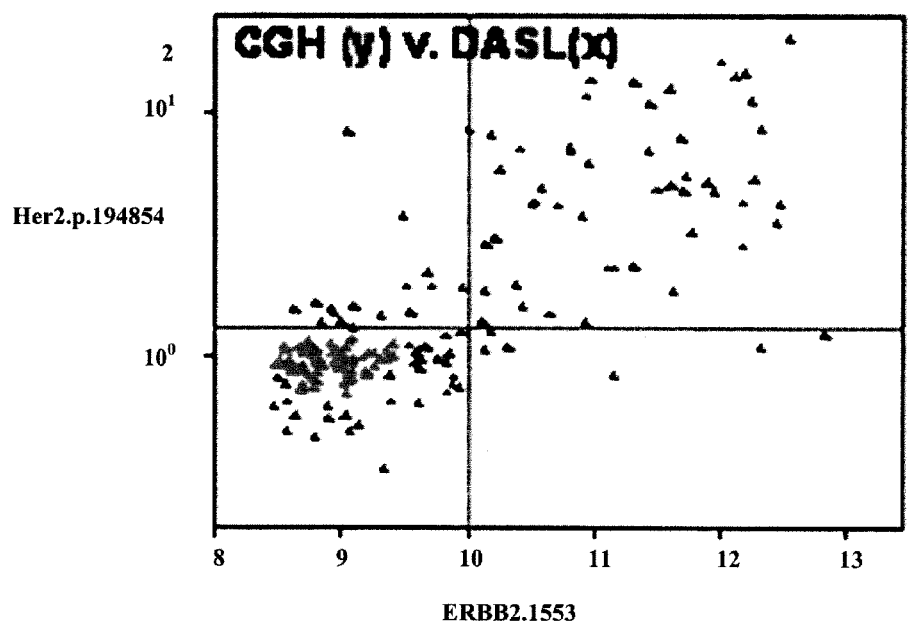
FIG. 4. Comparison of FISH, CGH and DASL Expression for ERBB2 (189 samples)
FIG. 4A. CGH (y) v. DASL (x)
FIG. 4B. FISH (y) v. DASL (x)
FIG. 4C. CGH (y) v. FISH (x)
FIG. 4D. DASL of CGH/FISH pos FIG. 5. Genotyping Distribution in 9840/9342 vs an Early Stage Cohort.
Figure 4B:
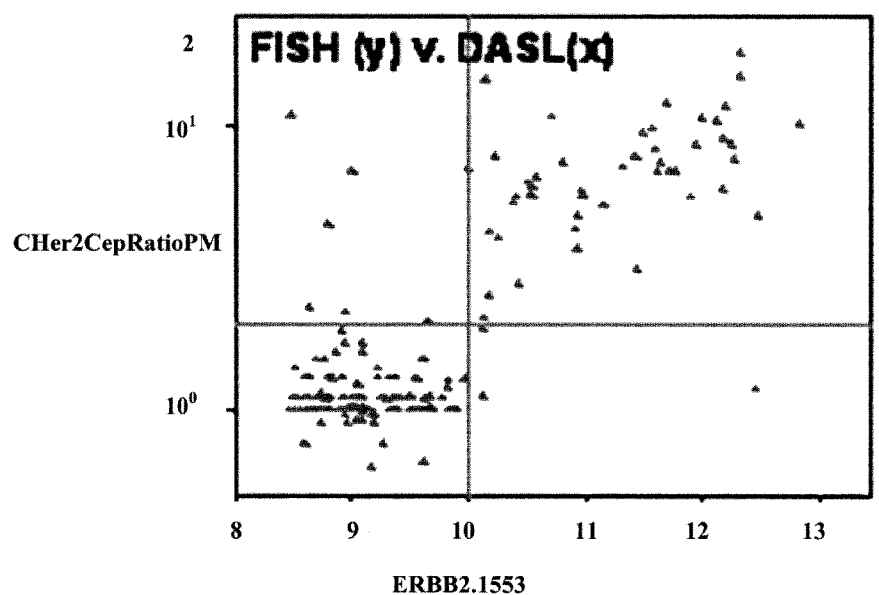
Figure 4C:
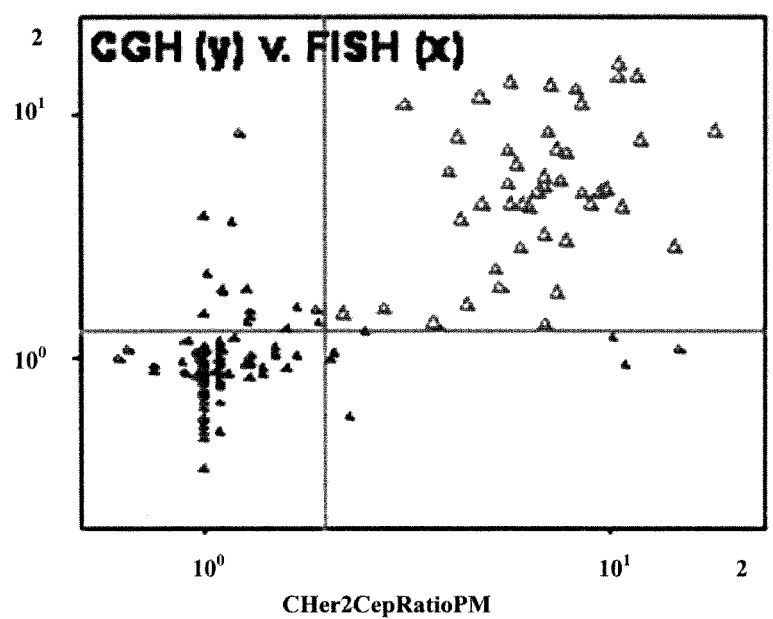
Figure 4D:
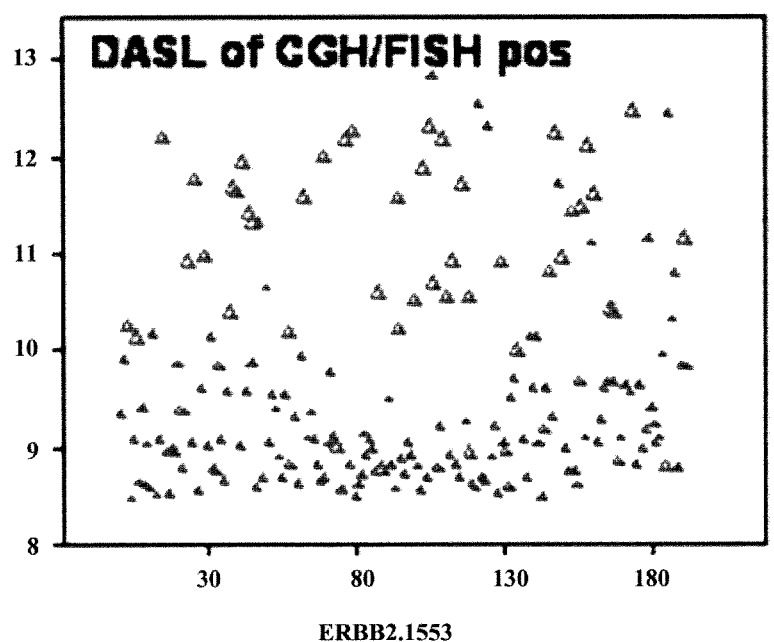
Figure 6A:
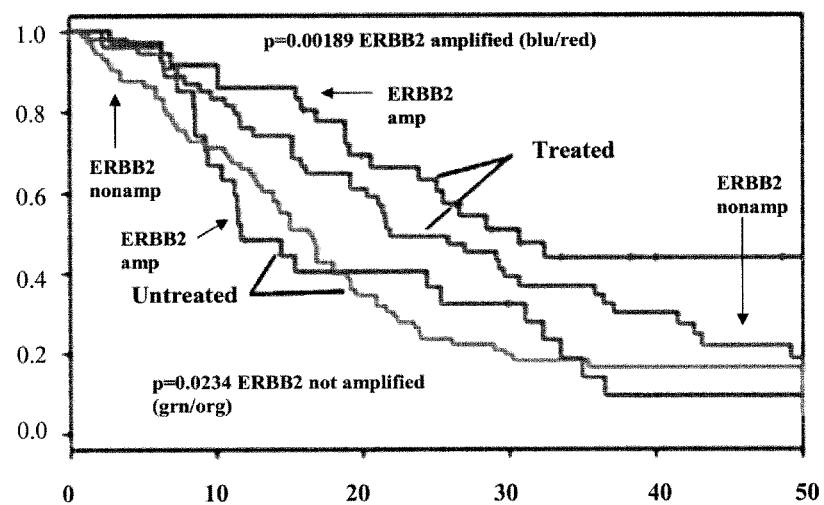
FIG. 6A. Trastuzumab extends survival (y axis) measured over months (x axis) for both ERBB2 amplified ("ERBB2 amp") and NON-amplified cases ("ERBB2 nonamp").
Figure 6B:
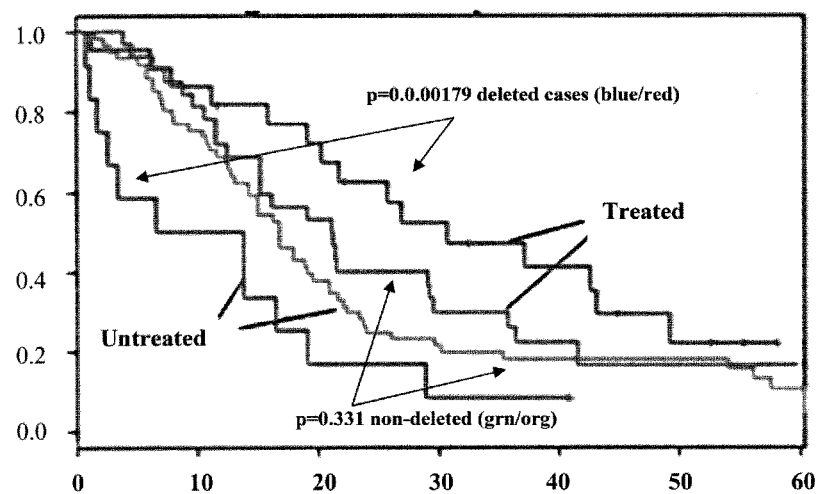
FIG. 6. CGH events that detect Trastuzumab responders among the ERBB2 NON-amplified cases.
FIG. 6C. Duplication of 4q(term) identifies increased Trastuzumab response among cases NOT amplified for ERBB2. Survival (y axis) measured over months (x axis).
FIG. 6D. Combining ERBB2 amp and NONamp carrying second marker treats more cases (87) than ERBB2 amp alone (53). Survival (y axis) measured over months (x axis).
Figure 6C:
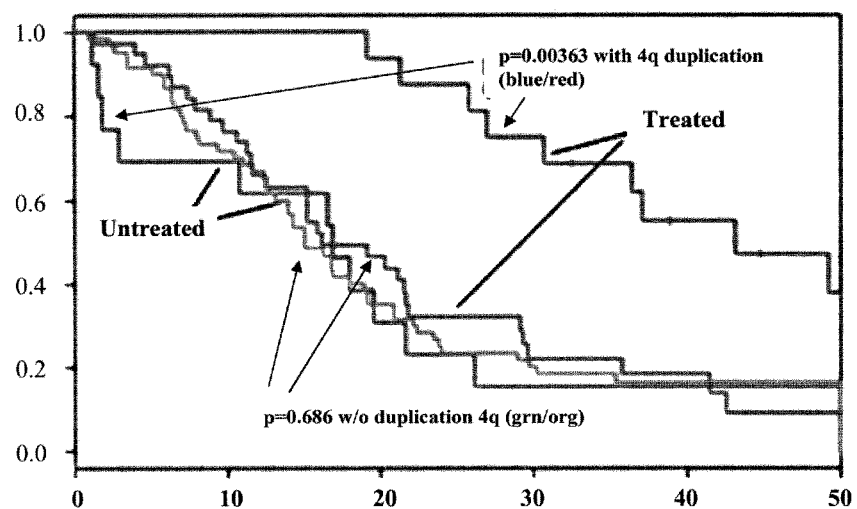
Figure 6D:
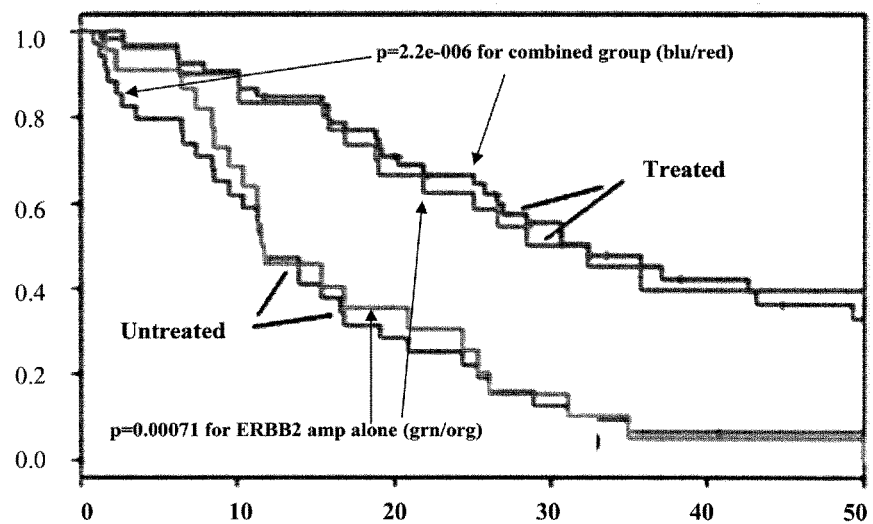
Figure 7A:
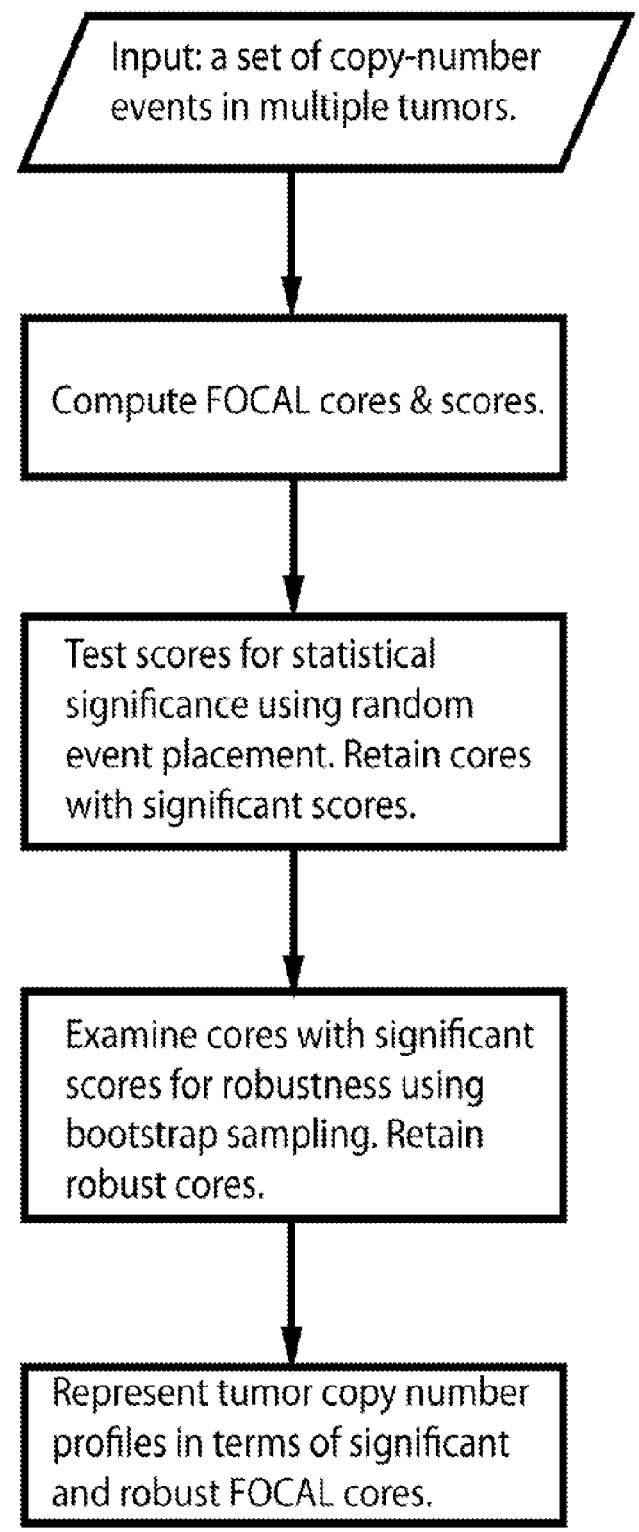
FIG. 7. Finder of Consistently Aberrant Loci (FOCAL)
FIG. 7A. Flowchart of FOCAL
FIG. 7B. Explanations provided by interval I to events $A_1$, $A_2$, $A_3$.
FIG. 7C. Main iteration loop of FOCAL for a set of four events (thick black horizontals). Five possible intersections are shown by thick gray horizontal lines. Thin gray lines show how the unexplained portions are updated assuming that C is the optimal explaining interval for the set.
Figure 7B:
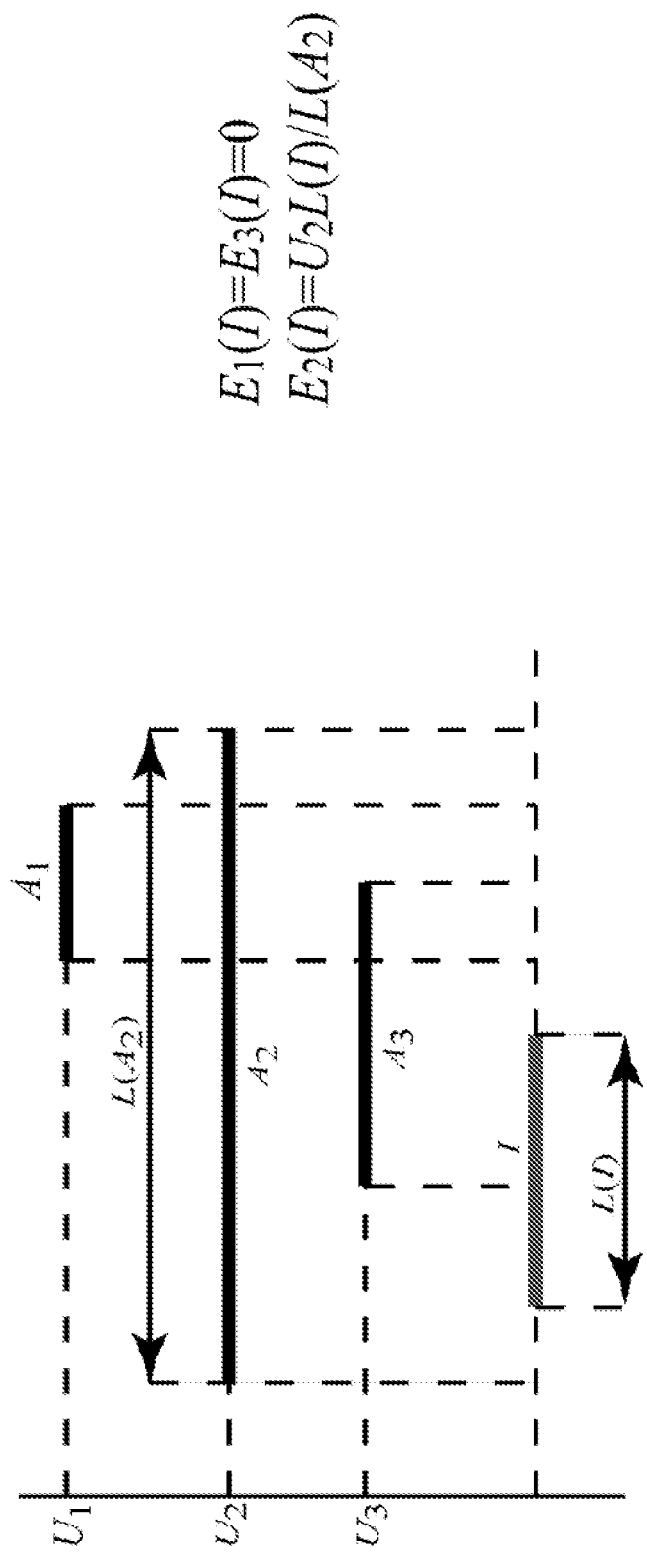
Figure 7C:
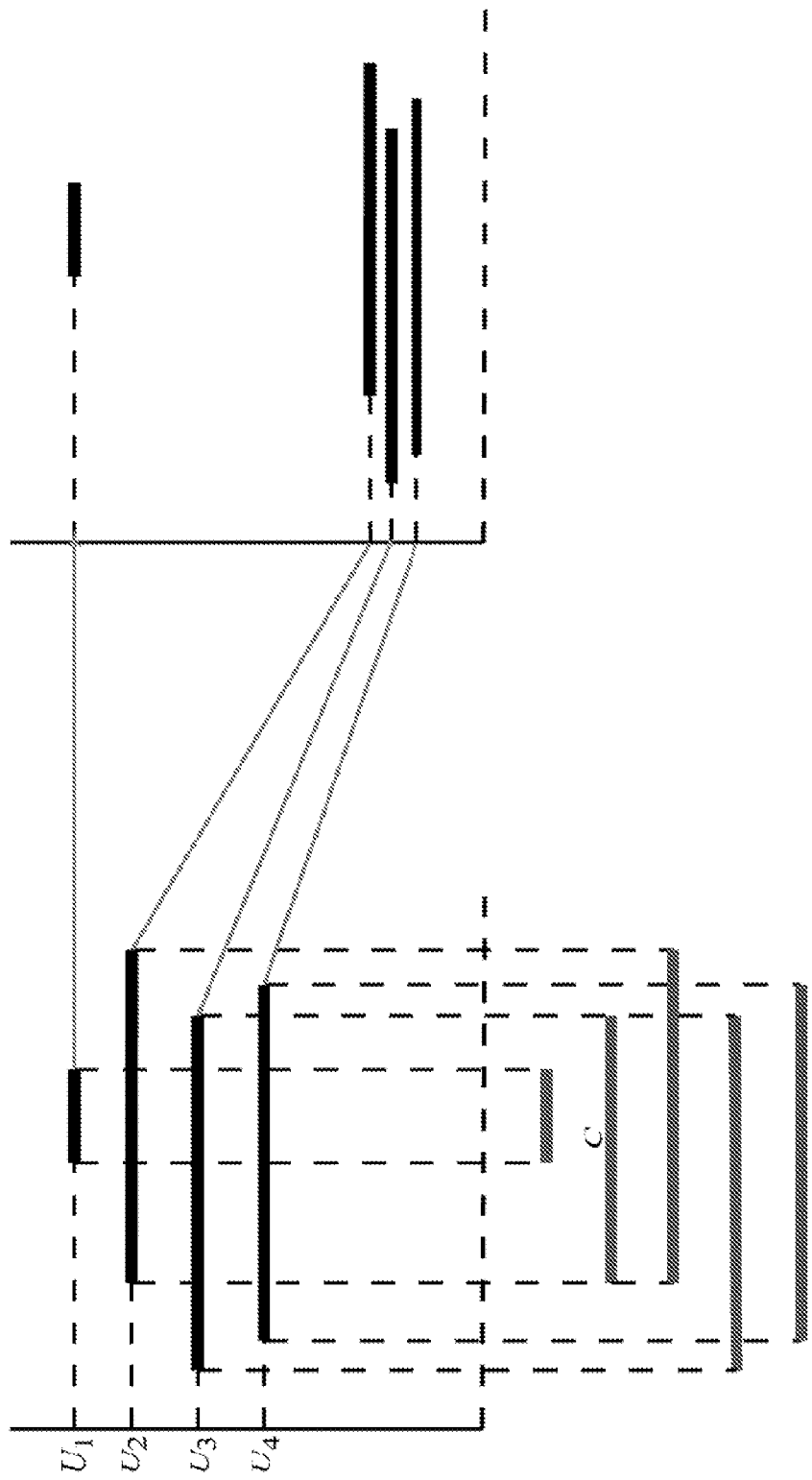
Figure 8:
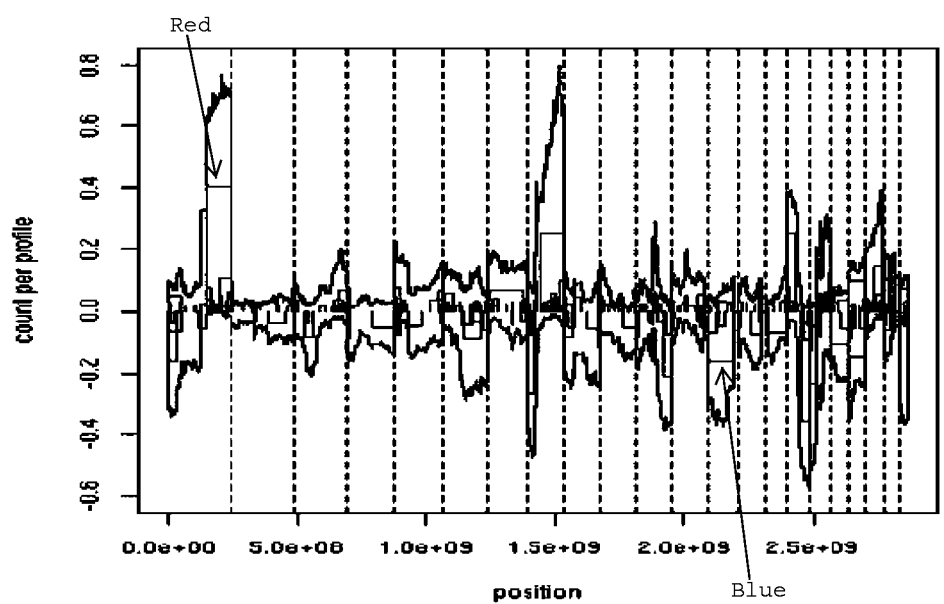
FIG. 8. Amplification and deletion consistently recurrent loci (CRLs) derived from a set of 257 breast tumor copy number profiles are shown at their genomic positions. The height (depth) of each CRL is its score per profile. Position-dependent amplification and deletion event counts per profile are shown for comparison. Chromosome boundaries are indicated by dashed verticals.

Kaplan-Maeier style curves for plotting survival (FIGS. 1-3) were obtained using the "survfit" and "survplot" functions in the statistical package that comes standard in the S-plus 2000 mathematical analysis software (sold by MathSoft, Inc.). Mulitvariate and univariate analysis of marker combinations was performed with the S-plus 2000 package or the freeware package known as "R".

Example 4

Results

Whole genome copy number data obtained using comparative genomic hybridization (CGH) was used for two purposes. The first analysis was to show that a microarray copy number procedure could yield results comparable to FISH for the purpose of determining the amplification status of the ERBB2 gene locus itself. Although both FISH and CGH both yield some false positives or false negatives when compared directly (FIG. 1A), the survival and recurrence curves for the two assays are statistically indistinguishable when used to determine which patient should receive trastuzumab (Herceptin®) (FIG. 2B). This shows that CGH by itself could be used as a predictive marker for success in trastuzumab therapy in Stage 4 breast cancer patients.

Secondly, a specific set of CGH values from the Her2 locus as well as certain locations in the genome not linked in any way to Her2 can be used in combination with the Her2 amplification value to identify a subset of patients, not previously anticipated to respond to trastuzumab (that is, those with low levels of Her2 mRNA and no amplification at the ERBB2 genetic locus) do, in fact, respond to trastuzumab in a statistically significant manner.

This is a targeted approach based on examination of frequency plots of subpopulations of this cohort to identify 10 potential regions that might affect trastuzumab sensitivity, rather than a whole genome based study. Therefore the correction for multiple testing (Bonfaroni correction) is limited to less than one log 10.

Univariate analysis of these markers yields the following hazard ratios. Those in numbers 4 and 5 are comparable to the treatment benefit of patients with ERBB2 amplification.

1. There is a significant benefit of trastuzumab treatment in the entire cohort. The non-treatment hazard is 1.504, meaning that the non-treated patients are 1.504 many times likely to fail within a month from now provided that they have survived till now.
2. For those with ERBB2 amplification using either the CGH or FISH threshold there is more benefit from treatment: the non-treatment hazard is 2.09.

An amplification at marker B: A ratio of 1.1 or greater (when compared to a known diploid reference genome) for any genomic location bounded by the following chromosomal positions on human chromosome 4q (defined by the reference genome in the UCSC genome browser reflecting freeze HG18):

Position 169.81 mb-185.239 mb on 4q. The genomic location bounded by position 169.81 mb-185.239 mb on human chromosome 4q (beginning at 4q169.81 and ending at 4q185.239) as defined by the reference genome in the UCSC genome browser reflecting freeze HG18 is set forth in SEQ ID NO:1.

The reference genome referred to as freeze HG18 is the March 2006 human reference sequence (NCBI Build 36.1) which was produced by the International Human Genome Sequencing Consortium (Nature. (2001) February 15; 409 (6822):860-921; Kuhn et al., "The UCSC Genome Browser database: update 2007." Nucleic Acids Res. (2007) January; 35(Database issue):D668-D673; Fujita et al., "The UCSC Genome Browser database: update 2011." Nucleic Acids Res. (2011) 39 (suppl 1): D876-D882.) The HG18 reference genome data is publicly available at: genome.ucsc.edu/cgi-bin/hgGateway?db=hg18

Table 1 shows the chromosomal coordinates for ErbB2 and markers B, D1, and D2, in addition to the P-values obtained when patients positive for deletion at marker D1, deletion at marker D2, and amplification at marker B were treated with trastuzumab. The number of patients affected and hazard ratios are also displayed.

TABLE 1

| Marker | Central Probe | Chrom | Chrompos. Center (Mb) | Chrompos Start (Mb) | Chrompos End (Mb) | P value | Patients affected | Hazard Ratio |
|---|---|---|---|---|---|---|---|---|
| ERBB2 | 194854 | 17q | 35.16 | 34.89 | 35.25 | 0.003 | | 2.09 |
| D1 | 195350 | 17q | 38.54 | 35.42 | 56.76 | 0.00048 | 30/206 | 2.457 |
| D2 | 194554 | 17q | 33.461 | 32.010 | 34.215 | $4 \times 10^{-6}$ | 33/206 | 2.7 |
| B | 66000 | 5q | 176.587 | 169.81 | 185.239 | 0.029 | 28/206 | 1.79 |

3. For those with no ERBB2 amplification the benefit from treatment is not significant.
4. For those with no ERBB2 amplification but with a deletion at probe 195350 (Marker D1) the non-treatment hazard is 2.457.
5. For those with no ERBB2 amplification and no deletion at probe 66000 (Marker B) the non-treatment hazard is 1.793.

These predictive markers, obtained from CGH data, can be defined as follows:

A deletion at marker D1: A CGH ratio (when compared to a known diploid reference genome) of 0.85 or less for any genomic location bounded by the following chromosomal positions (in megabasepairs) on human chromosome 17q (defined by the reference genome in the UCSC genome browser reflecting freeze HG18):

Position 36.100 mb-38.6 mb on 17q

A deletion at marker D2: A ratio (when compared to a known diploid reference genome) of 0.85 or less for any genomic location bounded by the following chromosomal positions on human chromosome 17q (defined by the reference genome in the UCSC genome browser reflecting freeze HG18):

Position 33.361 mb-33.8 mb on 17q

Example 5

FOCAL

Methods 226 copy number profiles were obtained as described in Example 3. Single-profile pre-processing included normalization, segmentation, and identification of significantly aberrant segments (amplification and deletion events). Candidate markers were identified using the FOCAL (Finder of Consistently Aberrant Loci) algorithm, defined for amplifications as follows. The definition for deletion is completely analogous.

FOCAL is a computational and statistical method for identifying regions of recurrent and consistent DNA copy number alteration in a set of multiple copy number profiles. The input into FOCAL is a joint set of N copy number events $A_j$, j=1, ..., N of a given sign (either amplifications or deletions) from all the profiles. Each event is associated with a specific interval of the genome and an additional attribute, a real number $U_j$, $0 \leq U_j \leq 1$, which is called the unexplained portion. Initially $U_j$ is set to 1 for all j. i.e., the events are considered completely unexplained. The algorithm examines genomic regions (intervals) for their ability to explain events as follows. For an event $A_j$ and an interval I the explanation $E_j(I)$ of $A_j$ by I is defined as $U_j L(I)/L(A_j)$ if I is contained in $A_j$ and as 0 otherwise, where, for any interval I. L(I) is its length. The explanation of the set of events by I is then computed by summing over the explanations of individual events: $E(I)=\Sigma_j E_j(I)$. FOCAL iteratively searches the genome for optimal explaining intervals. The iteration loop consists of two steps.

1. Compute the optimal explanation $S=\max_I E(I)$ of the event set and the corresponding optimal explaining interval $C=\text{argmax}_I E(I)$. These are called the FOCAL score and the FOCAL core, respectively.
2. Update the unexplained portions of the events by subtracting the explanations provided by C: $U_j \leftarrow U_j - E_j(C)$ for all $j=1, \ldots, N$.

It is evident that the optimal explaining interval is found among all possible non-empty intersections of events: for any interval I $E(I) \leq E(\Im)$, where $\Im$ is the intersection of all events in which I is contained.

Executing the main FOCAL loop results in a series of cores with scores in a decreasing order. Next, cores are selected whose scores are statistically significant and whose boundaries are robust against variations of the input data. The score significance is determined by empirically testing the null hypothesis that the observed kth FOCAL score is not improbable in a set of copy number profiles, each generated from an original profile by randomly placing its events in the genome. If K+1 is the smallest k for which the null hypothesis cannot be rejected, the first K cores are retained.

Robust cores are selected by applying FOCAL to multiple bootstrap samples of the original set of profiles. The first K cores are computed for each sample. These are matched to the original K cores. The degree of matching is quantified by the Jaccard index of the two intervals: $J_{CC'}=L(C \cap C')/L(C \cup C')$. These indices form a K×K matrix J. Matches are required to be mutually optimal: an original core C and a bootstrap-generated core C' are considered a match if $J_{CC'}$ is maximal in its respective column and row of J. If such mutually optimal matching can be found for an original core C and a bootstrap sample B, the corresponding $J_{CC'}$ is taken to be the matching score of C for B: $M_B(C)=\max_{C'} J_{CC'}$. Otherwise we set $M_B(C)=0$. Finally, a threshold T is introduced, $0 \leq T \leq 1$, and the reproducibility score of core C is defined as the fraction of bootstrap samples B in which $M_B(C)$ exceeds T.

It was determined that the first K=250 cores for each sign of aberration (amplification or deletion) are statistically significant at p=0.001 level. In view of growing computational cost computation beyond K=250 was not pursued. We then set T=0.6 and retained 188 amplification and 177 deletion cores whose reproducibility scores were above 0.75. All these were found among the first 226 amplification and 232 deletion cores. The number of retained cores is therefore limited by reproducibility rather than by significance.

Results

Twenty two markers were identified such that HER-negative, marker-positive subset contained no less than 10 profiles of trastuzumab-treated patients and no less than 10 profiles of trastuzumab-untreated patients.

Log-rank test for the effect of trastuzumab on overall survival was performed in each of the marker-positive, HER2-negative subsets. Hypothesis multiplicity was accounted for by estimating the false-discovery rate through a permutation test: each of the observed time-status-treatment triples of variables was assigned to a profile at random with no replacement. 1000 permutations were generated.

The top two markers (false discovery rate was estimated at 0.054) were identified as a loss of chromosome 18 (marker D3) and a broad deletion in chromosome 17 (marker D31). For these two markers the benefit was shown to be marker-specific: hazard ratios for trastuzumab were found to be significantly higher in the deletion-positive. HER2-negative subset than in the deletion-negative. HER2-negative subset in each case.

Deletions at markers D3 and D31 can be defined as follows:

Deletion at marker D3: A CGH ratio (when compared to a known diploid reference genome) of 0.85 or less for any genomic location bounded by the following chromosomal positions on human chromosome 18q (defined by the reference genome in the UCSC genome browser reflecting freeze HG18):

Position 2569041604-2644838637

Deletion at marker D31: A ratio (when compared to a known diploid reference genome) of 0.85 or less for any genomic location bounded by the following chromosomal positions on human chromosome 17q (defined by the reference genome in the UCSC genome browser reflecting freeze HG18):

Position 2491569515-2536157424

TABLE 2

| Marker | Chrom | Chrompos Start | Chrompos End | HR+ | Coxp+ | LRp+ | FDR+ | HR− | Coxp− | LRp− | p+− |
|---|---|---|---|---|---|---|---|---|---|---|---|
| D3 | 18 | 309355 | 76106388 | 6.37 | .0012 | .00028 | 0.054 | 2.60 | .094 | .092 | .008 |
| D31 | 17 | 1612008 | 46199917 | 5.00 | .00073 | .00021 | .091 | 1.42 | 0.15 | 0.15 | .009 |

Legend:
HR+, Coxp+, LRp+, FDR+ - univariate Cox hazard ratio, Cox regression p-value, log-rank p-value and false discovery rate in the deletion-positive subset;
HR−, Coxp−, LRp−, FDR− - univariate Cox hazard ratio, Cox regression p-value and log-rank p-value in the deletion-negative subset;
p+− - p-value for the difference in the hazard ratios between the two subsets.

In the case of marker D3 a two-variable Cox regression for trastuzumab treatment (T) and estrogen receptor status (ER) finds both covariates to be significant. Likewise, a two-variable Cox regression for T and progesteron receptor status (PGR) finds both covariates to be significant. However, only T retains significance in a three-variable Cox regression for T, ER and PGR. In the case of marker D31 basal expression subtype indicator (B) is found to be a significant covariate, and the effect of T is stronger when adjusted for B. No other covariates were found to be significant in each case.

TABLE 3 adjustment for covariates

| marker | covariate | HR (T) | p (T) | HR (covariate) | p (covariate) | Log-rank p |
|---|---|---|---|---|---|---|
| D3 | ER | 4.44 | .0097 | 3.41 | .033 | 7e-05 |
| D3 | PGR | 3.77 | .029 | 3.51 | .039 | 5.9e-05 |
| D31 | B | 5.091 | .00068 | 0.395 | .021 | 6.3e-05 |

Both marker D3 and marker D31 contain narrower deletion markers that do not meet the criterion of there being at least 10 profiles for each value of T. However, once marker D3 and marker D31 have been identified as significant, the narrower markers may be considered in a logical OR combination with their respective parent markers. The effect of T on survival is enhanced if a deletion at marker D3 is combined with a deletion at marker D57 and if a deletion marker D31 is combined with a deletion at marker D58.

Deletions at markers D57 and D58 are defined as follows:

Deletion at marker D57: A ratio (when compared to a known diploid reference genome) of 0.85 or less for any genomic location bounded by the following chromosomal positions on human chromosome 18q (defined by the reference genome in the UCSC genome browser reflecting freeze HG18):

Position 2613556418-2644838637

Deletion at marker D58: A ratio (when compared to a known diploid reference genome) of 0.85 or less for any genomic location bounded by the following chromosomal positions on human chromosome 17q (defined by the reference genome in the UCSC genome browser reflecting freeze HG18):

Position 2526115306-2531562878

Additional markers D11, D26, A1, and A73 were identified using FOCAL. Deletions or amplifications at the markers are defined as follows:

A deletion at marker D11: A ratio (when compared to a known diploid reference genome) of 0.85 or less for any genomic location bounded by the following chromosomal positions on human chromosome 15q (defined by the reference genome in the UCSC genome browser reflecting freeze HG18):

Position 2321235462-2388879211

A deletion at marker D26: A ratio (when compared to a known diploid reference genome) of 0.85 or less for any genomic location bounded by the following chromosomal positions on human chromosome 8q (defined by the reference genome in the UCSC genome browser reflecting freeze HG18):

Position 1394335322-1422565813

An amplification at marker A1: A ratio of 1.1 or greater (when compared to a known diploid reference genome) for any genomic location bounded by the following chromosomal positions on human chromosome 11 (defined by the reference genome in the UCSC genome browser reflecting freeze HG18):

Position 1819233296-1819244477

An amplification at marker A73: A ratio of 1.1 or greater (when compared to a known diploid reference genome) for any genomic location bounded by the following chromosomal positions on human chromosome 11 (defined by the reference genome in the UCSC genome browser reflecting freeze HG18):

Position 1819233296-1819234328

TABLE 3

Markers identified using the FOCAL algorithm. HG18) genomic coordinates and chromosomal positions are given for each marker.

| Marker | Chromosome | HG18) start | HG18) end | Chromosome position start | Chromosome position end |
|---|---|---|---|---|---|
| D3 | 18 | 2569041604 | 2644838637 | 309355 | 76106388 |
| D11 | 15 | 2321235462 | 2388879211 | 20444124 | 88087873 |
| D26 | 8 | 1394335322 | 1422565813 | 2780282 | 31010773 |
| D31 | 17 | 2491569515 | 2536157424 | 1612008 | 46199917 |
| D57 | 18 | 2613556418 | 2644838637 | 44824169 | 76106388 |
| D58 | 17 | 2526115306 | 2531562878 | 36157799 | 41605371 |
| A1 | 11 | 1819233296 | 1819244477 | 5755441 | 5766622 |
| A73 | 11 | 1819233296 | 1819234328 | 5755441 | 5756473 |

Example 6

Materials and Methods 12-18 yo primary tumor blocks from 238 patients on CALGB 9840 and CALGB 9342 (sample size 710).

DNA and RNA extracted from 1.5 mm punch cores using the Ambion Recover-All Nucleic Acid Kit™. (Harris Lab)

Nucleic acid purity, quality and quantity measured by:
spectrophotometric analysis
Bioanalyzer RNA Integrity Number (RIN)
threshold cycle values of housekeeping genes (RPL13A and Actin).

successful extraction, amplification and hybridization of 210/238 DASL arrays.

Date of receipt of FFPE punch core, age of sample (eg. diagnosis 1995), study source (eg. 9342, 9840), processing technician, and reagent batch not associated with assay failure.

260/280 ratio was outside of the expectant range in 18/28 (64%) of the tailed cases, compared with 92/238 (39%) of the entire cohort.

28/238 (11.8%) failure rate on these archived, formalin-fixed, paraffin-embedded breast tumors, range in age from 12-18 years.

50% of failed cases also failed FISH

Methods—CGH (Hicks Lab)

237 samples supplied from CALGB
FFPE DNA prep Ambion Recover-All Nucleic Acid Kit™
50-100 ug DNA amplified by WGA (Sigma)
CGH on Agilent 244K arrays (205/237 pass QC)
189 with usable CGH and complete clinical Info
Segmentation using cbs segmentlon (Olshen, 2004)
KM and Epicenter Calculations done on segmented values

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09677139B2). An electronic copy of the "Sequence Listing" will also be available from the USPTO upon request and payment of the fee set forth in 37 CFR 1.19(b)(3).

What is claimed is:

1. A method of treating a human subject afflicted with a cancer that is determined to be responsive to trastuzumab therapy, comprising
    a) obtaining a biological sample that comprises cancer cells of the subject;
    b) determining whether a copy number of a human chromosome region beginning at 4q169.81 and ending at 4q185.239 as defined by reference to the freeze HG18 reference genome (SEQ ID NO:1) in the cancer cells is amplified, wherein determining the copy number is performed by contacting DNA extracted from the cancer cells with probes or primers so as to amplify the DNA, and determining if the copy number at region corresponding to reference region 4q169.81-q185.239 (SEQ ID NO:1) is amplified in the cancer cells compared to the copy number of region 4q169.81-q185.239 (SEQ ID NO:1) in a diploid reference;
    c) diagnosing the human subject to be afflicted with a cancer that is responsive to trastuzumab therapy if the human chromosome region corresponding to reference region 4q169.81-q185.239 (SEQ ID NO:1) in the cancer cells is amplified; and
    d) administering to the human subject diagnosed to be afflicted with a cancer that is responsive to trastuzumab therapy an amount of trastuzumab effective to treat the human subject.

2. The method of claim 1, wherein the subject is afflicted with a cancer, wherein the cells of the cancer overexpress HER2.

3. The method claim 1, wherein trastuzumab therapy is administered as a monotherapy.

4. The method of claim 1, wherein trastuzumab therapy is administered as an adjuvant therapy.

* * * * *

UNITED STATES PATENT AND TRADEMARK OFFICE
CERTIFICATE OF CORRECTION

| | |
|---|---|
| PATENT NO. | : 9,677,139 B2 |
| APPLICATION NO. | : 13/491359 |
| DATED | : June 13, 2017 |
| INVENTOR(S) | : James Hicks et al. |

It is certified that error appears in the above-identified patent and that said Letters Patent is hereby corrected as shown below:

In the Specification

At Column 1, Line 17 insert:
--This invention was made with government support under grant W81XWH-09-1-0591 awarded by Army Medical Research Materiel Command. The government has certain rights in the invention.--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*